US009888885B2

(12) United States Patent
An et al.

(10) Patent No.: US 9,888,885 B2
(45) Date of Patent: Feb. 13, 2018

(54) HANDLING VEHICLE ACCIDENTS USING A MOBILE TERMINAL

(71) Applicant: LG Electronics Inc., Seoul (KR)

(72) Inventors: Sungje An, Seoul (KR); Kwangjae Lee, Seoul (KR); Seungman Kim, Seoul (KR)

(73) Assignee: LG Electronics Inc., Seoul (KR)

( * ) Notice: Subject to any disclaimer, the term of this patent is extended or adjusted under 35 U.S.C. 154(b) by 77 days.

(21) Appl. No.: 14/727,991

(22) Filed: Jun. 2, 2015

(65) Prior Publication Data
US 2015/0342542 A1   Dec. 3, 2015

(30) Foreign Application Priority Data

Jun. 3, 2014   (KR) .......................... 10-2014-0067829

(51) Int. Cl.
H04M 11/04   (2006.01)
A61B 5/00   (2006.01)
(Continued)

(52) U.S. Cl.
CPC ............ *A61B 5/747* (2013.01); *A61B 5/0022* (2013.01); *A61B 5/02055* (2013.01);
(Continued)

(58) Field of Classification Search
CPC .............................. H04W 4/22; H04W 76/007
(Continued)

(56) References Cited

U.S. PATENT DOCUMENTS 5,729,205 A * 3/1998 Kwon .................. A61B 5/0002
340/471
2007/0016362 A1* 1/2007 Nelson ................. G01C 21/362
701/425
(Continued)

FOREIGN PATENT DOCUMENTS

CN   101722852   6/2010
CN   203086454   7/2013
(Continued)

OTHER PUBLICATIONS

Korean Notice of Allowance dated Sep. 22, 2015 for Korean Application No. 10-2014-0067829, 5 pages.
(Continued)

*Primary Examiner* — Chuck Huynh
(74) *Attorney, Agent, or Firm* — Fish & Richardson P.C.

(57) ABSTRACT

A mobile terminal includes a terminal body that is wearable on a part of a user's body. A wireless communication unit of the mobile terminal connects to an e-Call system of a vehicle and receives information related to a state of the vehicle. A detecting unit of the mobile terminal detects a biometric signal of the user that is sensed by at least one sensor provided in the terminal body. A controller is configured to, based on an accident event of the vehicle being detected from the received information related to the state of the vehicle, analyze the detected biometric signal to obtain state information of the user. Based on a predetermined condition being satisfied, the controller cooperates with the e-Call system of the vehicle and transmits the obtained state information of the user and the information related to a state of the vehicle to a call center.

18 Claims, 8 Drawing Sheets

(51) Int. Cl.
*G07C 5/00* (2006.01)
*G01S 19/13* (2010.01)
*H04M 1/725* (2006.01)
*H04B 1/3827* (2015.01)
*H04W 76/00* (2018.01)
*H04W 56/00* (2009.01)
*H04W 4/02* (2018.01)
*H04M 3/51* (2006.01)
*A61B 5/0205* (2006.01)
*G08B 25/01* (2006.01)
*G08B 25/10* (2006.01)
*G08B 25/14* (2006.01)
*G08B 29/06* (2006.01)
*A61B 5/053* (2006.01)
*A61B 5/01* (2006.01)
*A61B 5/024* (2006.01)
*A61B 5/021* (2006.01)

(52) U.S. Cl.
CPC ............ *A61B 5/7282* (2013.01); *G01S 19/13* (2013.01); *G07C 5/008* (2013.01); *G08B 25/016* (2013.01); *G08B 25/10* (2013.01); *G08B 25/14* (2013.01); *G08B 29/06* (2013.01); *H04B 1/385* (2013.01); *H04M 1/72538* (2013.01); *H04M 3/5116* (2013.01); *H04W 4/023* (2013.01); *H04W 56/001* (2013.01); *H04W 76/007* (2013.01); *A61B 5/01* (2013.01); *A61B 5/021* (2013.01); *A61B 5/024* (2013.01); *A61B 5/0533* (2013.01); *H04M 2242/04* (2013.01)

(58) Field of Classification Search
USPC .......................... 455/404.2, 404.1; 340/436
See application file for complete search history.

(56) References Cited

U.S. PATENT DOCUMENTS

| | | | | |
|---|---|---|---|---|
| 2013/0143519 | A1* | 6/2013 | Doezema | G08B 21/0446 455/404.2 |
| 2014/0300739 | A1* | 10/2014 | Mimar | H04N 7/188 348/148 |
| 2014/0309849 | A1* | 10/2014 | Ricci | B60Q 1/00 701/33.4 |
| 2015/0145662 | A1* | 5/2015 | Barfield, Jr. | G08B 25/016 340/436 |

FOREIGN PATENT DOCUMENTS

| | | |
|---|---|---|
| CN | 103342118 | 10/2013 |
| DE | 10 2007 042111 A1 | 3/2009 |
| JP | 5044140 | 10/2012 |
| KR | 2004-0073059 A | 8/2004 |
| KR | 2010-0036451 A | 4/2010 |
| KR | 10-2011-0113379 A | 10/2011 |
| KR | 10-1157864 B1 | 6/2012 |
| WO | WO 2005/098724 A2 | 10/2005 |

OTHER PUBLICATIONS

European Search Report dated Nov. 9, 2015 for European Application No. 15000409.1, 7 pages.
Korean Office Action dated Mar. 23, 2015 for Korean Application No. 10-2014-0067829, 5 Pages.

* cited by examiner

HANDLING VEHICLE ACCIDENTS USING A MOBILE TERMINAL

CROSS-REFERENCE TO RELATED APPLICATIONS

Pursuant to 35 U.S.C. § 119(a), this application claims the benefit of an earlier filing date and right of priority to Korean Application No. 10-2014-0067829 filed on Jun. 3, 2014, the contents of which are incorporated by reference herein in their entirety.

TECHNICAL FIELD

This application relates to a mobile terminal operating in association with an e-Call system of a vehicle.

BACKGROUND

Terminals may be generally classified as mobile/portable terminals or stationary terminals according to their mobility. Mobile terminals may also be classified as handheld terminals or vehicle mounted terminals according to whether or not a user can directly carry the terminal.

Mobile terminals have become increasingly more functional. Examples of such functions include data and voice communications, capturing images and video via a camera, recording audio, playing music files via a speaker system, and displaying images and video on a display. Some mobile terminals include additional functionality which supports game playing, while other terminals are configured as multimedia players. More recently, mobile terminals have been configured to receive broadcast and multicast signals which permit viewing of content such as videos and television programs.

SUMMARY

In one aspect, a mobile terminal includes a terminal body configured to be wearable on a part of a user's body. A wireless communication unit of the mobile terminal is configured to connect to an e-Call system of a vehicle and receive information related to a state of the vehicle. A detecting unit of the mobile terminal is configured to detect a biometric signal of the user that is sensed by at least one sensor provided in the terminal body. A controller is configured to, based on an accident event of the vehicle being detected from the received information related to the state of the vehicle, analyze the detected biometric signal to obtain state information of the user. Based on a predetermined condition being satisfied, the controller cooperates with the e-Call system of the vehicle and transmits the obtained state information of the user and the information related to a state of the vehicle to a call center.

In some implementations, the predetermined condition includes a condition in which a degree of impact corresponding to the obtained state information of the user exceeds a predetermined reference range or a condition in which a degree of impact corresponding to the received information related to a state of the vehicle exceeds a predetermined reference range.

In some implementations, the controller is further configured to periodically check a state of connection with the e-Call system and perform synchronization with the e-Call system. Based on a state of the connection, the controller provides the obtained state information of the user to the connected e-Call system.

In some implementations, the controller is configured to, based on an emergency signal included in the obtained state information of the user being detected, control the wireless communication unit to contact an external terminal nearest to a current location of the user by using a global positioning system (GPS) or a base station (BS).

In some implementations, the controller is further configured to, in response to a detected accident event of a vehicle: periodically obtain state information of the user, and based on the predetermined condition being satisfied, transmit a message to the call center to allow the user to be provided with an accident handling service varied according to a degree of impact corresponding to the periodically obtained state information of the user.

In some implementations, the controller is configured to, after an accident event of the vehicle is detected and based on an abnormal signal of state information of the user obtained at a second point in time being greater than an abnormal signal of state information of the user obtained at a first point in time, transmit a message to the call center to induce the vehicle to stop running.

In some implementations, the controller is configured to, after an accident event of a vehicle is detected and based on detecting that an abnormal signal of state information of the user obtained at a second point in time is maintained or is smaller than the abnormal signal of state information of the user obtained at a first point in time, transmit a message to the call center to induce the call center to determine a medical institution nearest to a current location of the vehicle.

In some implementations, the wireless communication unit is further configured to receive, from the connected e-Call system, image data that was imaged before and after the detected accident event. The controller is further configured to, based on the predetermined condition being satisfied, transmit the state information of the user, the information related to a state of the vehicle, and the received image data to the call center.

In some implementations, the at least one sensor provided in the terminal body includes at least one or more of a galvanic skin response (GSR) sensor, a body temperature sensor, a pulse sensor, or a pressure sensor.

In some implementations, the controller is configured to detect an accident event by performing operations that include: determining whether the vehicle has been in an accident based on the received information related to a state of the vehicle, and in response to determining that the vehicle has been in an accident based on the received information related to a state of the vehicle, confirming that the vehicle has been in an accident using the biometric signal.

In some implementations, the mobile terminal also includes an output unit provided in the terminal body and configured to output vibrations. The controller is configured to, in response to the accident event of the vehicle being detected based on the received information, control the output unit to output a vibration with a predetermined pattern.

In some implementations, the controller is further configured to provide a control signal such that the state information of the user is provided, through the call center, to a medical server that interworks with the call center, and receive an accident handling service that is varied according to diagnosis results provided by the medical server based on the state information of the user.

In some implementations, the state information of the user is represented by a plurality of stages indicating different levels of severity.

In some implementations, the predetermined condition includes a condition in which the state information of the user indicates an emergency situation and the received information related to a state of the vehicle does not indicate an accident of the vehicle, and the mobile terminal is configured to transmit a message to a device external to the vehicle based on the state information of the user indicating an emergency situation.

In some implementations, the device external to the vehicle is a mobile device of another user.

In another aspect, a method handles an accident of a vehicle. The method includes connecting a mobile terminal to an e-Call system of a vehicle and receiving, at the mobile terminal, information related to a state of the vehicle from the e-Call system. The method also includes detecting a biometric signal of a user who is wearing the mobile terminal, and based on an accident event of the vehicle being detected from the received information related to a state of the vehicle, analyzing the detected biometric signal of the user to obtain state information of the user. The method further includes, based on a predetermined condition being satisfied by the obtained state information of the user and the information related to a state of the vehicle, transmitting to a call center, by the mobile terminal in cooperation with the e-Call system, the obtained state information of the user and the information related to a state of the vehicle.

In some implementations, the predetermined condition includes a condition in which a degree of impact corresponding to the obtained state information of the user exceeds a predetermined reference range or a condition in which a degree of impact corresponding to the received information related to a state of the vehicle exceeds a predetermined reference range.

In some implementations, the method also includes periodically checking a state of connection with the e-Call system and performing synchronization with the e-Call system. Based on a state of the connection, the method provides the obtained state information of the user to the connected e-Call system.

In another aspect, a system includes an e-Call system installed in a vehicle, and a mobile terminal configured to be wearable on a part of a user's body. The mobile terminal includes a wireless communication unit configured to connect to the e-Call system of the vehicle and receive information related to a state of the vehicle, and a detecting unit configured to detect a biometric signal of the user. A controller is configured to, responsive to an accident event of the vehicle being detected from the received information related to a state of the vehicle, obtain state information of the user based on analyzing the biometric signal detected by the detecting unit of the mobile terminal. The controller also determines that a predetermined condition is satisfied by at least one of the state information of the user or the received information related to the state of the vehicle, and based on determining that the predetermined condition is satisfied, cooperates with the e-Call system of the vehicle and transmits, to a call center, at least one of the state information of the user or the information related to a state of the vehicle.

In some implementations, the system also includes a second mobile terminal configured to be wearable on a part of a second user's body. The second mobile terminal includes a second wireless communication unit configured to connect to the e-Call system of the vehicle and receive information related to a state of the vehicle, and a second detecting unit configured to detect a biometric signal of the second user. The controller is further configured to analyze the biometric signal of the second user to determine state information of the second user. The predetermined condition further depends on the state information of the second user.

All or part of the features described throughout this application can be implemented as a computer program product including instructions that are stored on one or more non-transitory machine-readable storage media, and that are executable on one or more processing devices. All or part of the features described throughout this application can be implemented as an apparatus, method, or electronic system that can include one or more processing devices and memory to store executable instructions to implement the stated functions.

The details of one or more implementations are set forth in the accompanying drawings and the description below. Other features will be apparent from the description and drawings, and from the claims. The description and specific examples below are given by way of illustration only, and various changes and modifications will be apparent.

DETAILED DESCRIPTION

Figure 1:
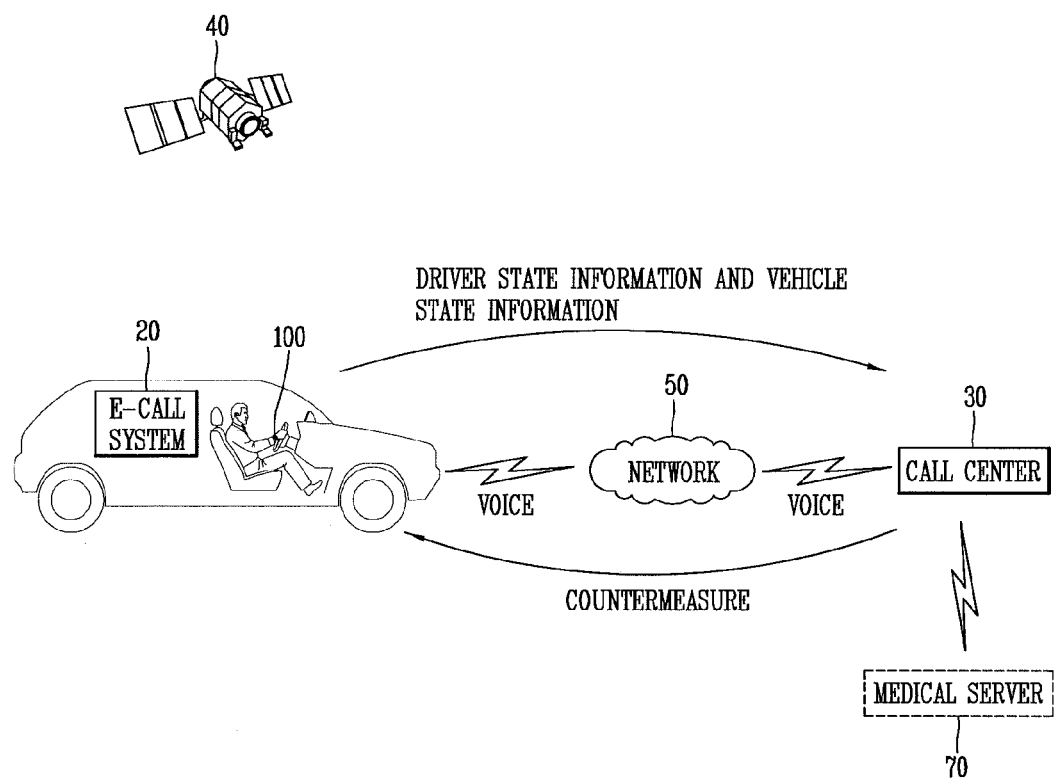
FIG. 1 is a sketch illustrating an example of a system in which a mobile terminal may operate.

A system obtains biological information regarding a user within a vehicle (e.g., a driver and/or a passenger of the vehicle), as well as information regarding a state of the vehicle, and based on analyzing the information, contacts one or more external devices/systems regarding the state of the user and/or the state of the vehicle. In some implementations, the system provides the obtained state information and/or information regarding a determined emergency state to one or more devices external to the vehicle. In some implementations, the system communicates with a call center by interworking with an e-Call system installed within the vehicle. In some implementations, the information may be provided to a medical server that may provide emergency services to the user.

The system includes a mobile terminal (e.g., a wearable device worn by a user) that monitors biological (e.g., biometric) signals of the user, as well as an e-Call system installed in the vehicle that monitors a state of the vehicle. Based on the information of the user and/or the vehicle, the system determines a condition of the passenger and/or the vehicle and determines whether to contact a call center using the e-Call system. For example, when a vehicle accident occurs, and/or when a driver/passenger of the vehicle is in a dangerous state, the system may detect this condition and contact the e-Call center, or take other suitable actions.

In some implementations, the system includes a mobile terminal that is capable of obtaining state information of a driver and/or a passenger of a vehicle and providing the obtained state information to a call center, when a vehicle accident occurs, whereby an emergency rescue service varied according to a situation may be received. For example, the emergency rescue service may be varied according to a severity level of the user, as determined from the analyzed biological information of the user and/or the vehicle information.

In some implementations, the mobile terminal may be a wearable device, such as a watch-type, necklace-type, bracelet-type, or ring-type mobile terminal that contacts with part of a user body. In some implementations, the mobile terminal may be installed in clothing that is worn by a user, or installed on a part of the vehicle that the user handles (e.g., a steering wheel).

In some implementations, the mobile terminal may be communicative with a system of a vehicle or other external devices/systems. For example, the vehicle may have installed an emergency call system, such as an e-Call system, that may be able to automatically send a rescue signal when a dangerous condition is detected. For example, when an emergency occurs with the vehicle (e.g., an accident), the e-Call system may detect the dangerous condition and transmit information such as current location, destination, moving direction of a vehicle, or other information, to an emergency rescue institution or other agency.

In some implementations, the system may also detect a dangerous condition of a user in the vehicle (e.g., a driver or a passenger) and transmit a signal (e.g., via the e-Call system or some other communication medium). As such, the system may detect that a user (e.g., a driver or a passenger of the vehicle) is in a dangerous state and automatically contact an emergency rescue institution, even if it may be physically difficult for the driver or the passenger to communicate with the emergency rescue institution regarding his/her condition.

In some implementations, biological information related to two or more users in the vehicle may be received from multiple mobile terminals worn by the users, and the aggregate biological information may be analyzed to determine whether an accident has occurred and/or a severity level of the accident. In some implementations, even if the vehicle's e-Call system does not detect an accident event, the biological information from one or more users may be analyzed to determine that an emergency situation exists, and one or more mobile terminals may separately contact an external device/system based on the analyzed biological information (separate from the e-Call system).

Description will now be given in detail according to some implementations disclosed herein, with reference to the accompanying drawings. For the sake of brief description with reference to the drawings, the same or equivalent components may be provided with the same or similar reference numbers, and description thereof will not be repeated. The accompanying drawings are used to help easily understand various technical features and the implementations presented herein are not limited by the accompanying drawings. As such, the present disclosure should be construed to extend to any alterations, equivalents and substitutes in addition to those which are particularly set out in the accompanying drawings.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element.

FIG. 1 is a sketch illustrating an example of an environment in which a system may operate.

As illustrated in the example of FIG. 1, a mobile terminal 100 may be implemented as a watch-type mobile terminal 100 that may be worn on a particular part of a body of a driver in a vehicle, for example, on a wrist. Also, the watch-type mobile terminal 100 may be connected to an e-Call system 20 installed in a vehicle.

In this example, the e-Call system 20 is an emergency call system for transmitting information, such as a current location, state, or the like, of a vehicle, to an emergency rescue agency when an emergency, such as a car accident, or the like, occurs. The e-Call system 20 may be implemented through a telematics device installed in a vehicle, for example. Hereinafter, for the purposes of description, an e-Call system 20 using a telematics device installed in a vehicle will be described as an example.

The watch-type mobile terminal 100 and the e-Call system 20 may be connected using a suitable communication mechanism, for example, a near-field communication standard such as Bluetooth, or the like, a wireless Internet standard such as Wi-Fi, or the like, an external device interface standard such as a universal serial bus (USB), or the like, etc.

In some implementations, the e-Call system 20 may be associated with one or more sensors provided in a vehicle, for example, a sensor for sensing inflation of an airbag, an impact sensor, or the like, to sense an accident of a vehicle. In some implementations, the e-Call system 20 may transmit a location and state information of the vehicle to a predetermined external device/system, such as call center 30 in FIG. 1, through a communication medium (e.g., network 50, satellite 40, etc.) in response to the sensed accident.

In some implementations, information regarding the sensed accident of the vehicle using the e-Call system 20 is delivered to the wirelessly connected watch-type mobile terminal 100. The watch-type mobile terminal may additionally collect information regarding the user. For example, a biological signal of the wearer may be detected before and after the accident and analyzed using various sensors (for example, a GSR sensor, a body temperature sensor, a pulse sensor, a pressure sensor, or the like) provided in the terminal body of the watch-type mobile terminal 100. The watch-type mobile terminal 100 may provide various types of information related to the generated accident of the vehicle according to the analysis result of the biological signal.

In some implementations, the watch-type mobile terminal 100 may recognize a degree of impact of the wearer in the accident according to the analysis results of the biological signal. As a particular example, when the watch-type mobile terminal 100 is worn on the driver, a cause of the accident (drowsy driving, stress, or the like) may be recognized based on the analysis results of the biological signal prior to the accident. Also, the watch-type mobile terminal 100 may periodically detect a biological signal of the wearer after the accident to recognize information related to a change in a state of the wearer.

In some implementations, when a predetermined condition is met, the watch-type mobile terminal 100 interworks with the e-Call system 20 to transmit state information corresponding to the analysis of the biological signal of the wearer to the call center 30.

Then, the call center 30 may automatically recognize a state of a driver or a passenger within the vehicle when vehicle accident occurs, as well as a location and a state of the vehicle in the accident. In response, the call center 30 may perform a suitable action, such as establishing a call connection to the e-Call system 20 of the vehicle or the watch-type mobile terminal 100 to inquire about a situation related to the generated accident, or guiding a service related to emergency rescue measures. In particular, in relation to the emergency rescue measures, even in an emergency situation in which the driver or the passenger in the accident cannot directly call the call center 30, state information of the vehicle driver or the driver or the passenger may be automatically generated by the user's mobile terminal 100 and/or the vehicle's e-Call system 20, and received by the e-Call center 30. Thus, emergency measures that are appropriate for the driver or the passenger in the accident may be taken without necessarily requiring the user to take explicit action.

In some implementations, the call center 30 may interwork with a medical server 70 to perform diagnosis corresponding to state information of the vehicle driver or the passenger and provide diagnosis results to the call center 30. The call center 30 may take a countermeasure initially based on the received diagnosis results.

Also, the watch-type mobile terminal 100 and the e-Call system 20 of the vehicle periodically check a connection state and perform synchronization. Thus, a biological signal of the driver or the passenger of the vehicle obtained through the watch-type mobile terminal 100 may be provided to the e-Call system 20 and information related to a state of the vehicle obtained through the e-Call system 20 of the vehicle may be provided to the watch-type mobile terminal 100.

Figure 2:
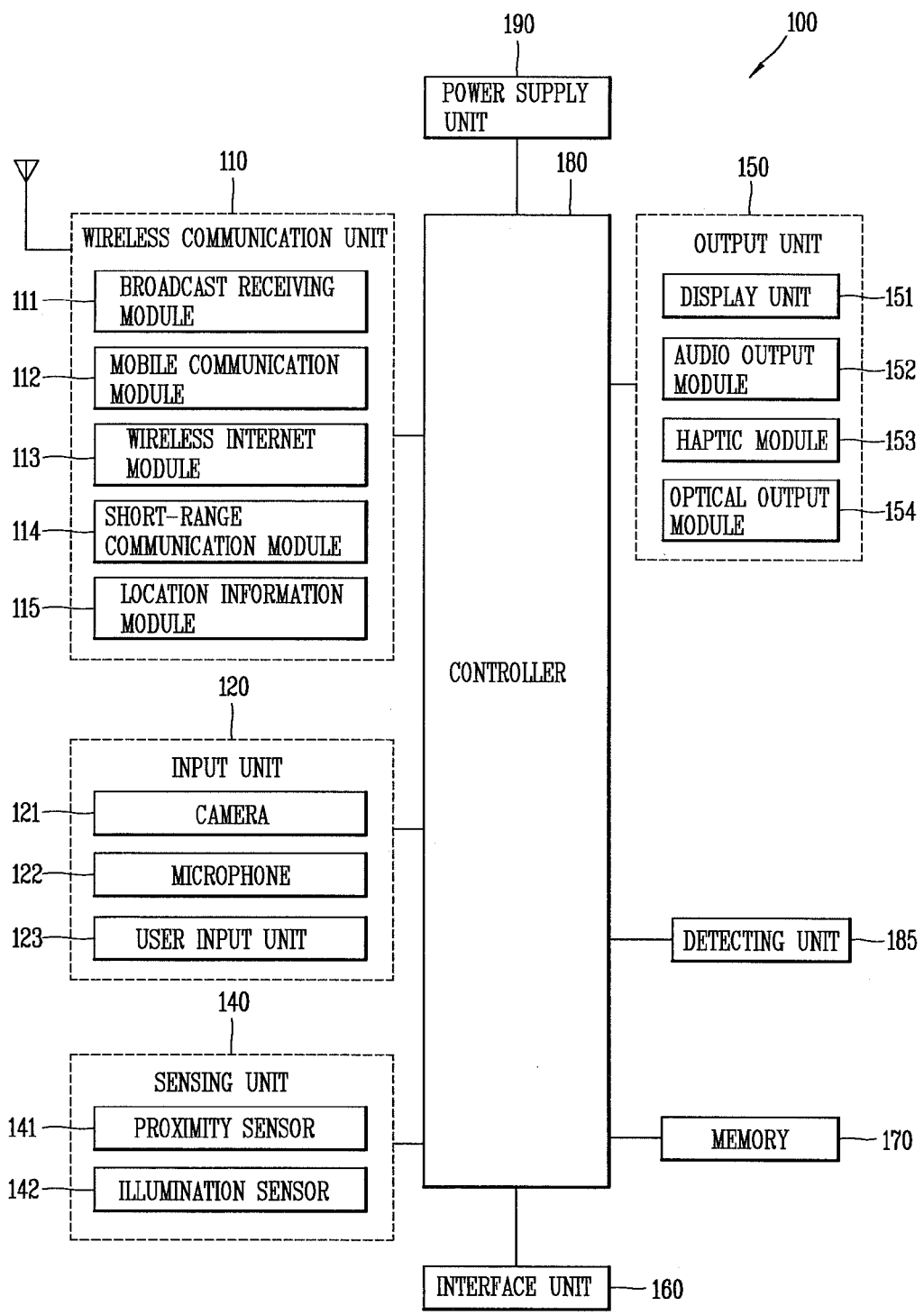
FIG. 2 is a block diagram illustrating an example of a mobile terminal.

FIG. 2 is a block diagram illustrating a configuration of the mobile terminal. The mobile terminal 100 is shown having components such as a wireless communication unit 110, an input unit 120, a sensing unit 140, an output unit 150, an interface unit 160, a memory 170, a controller 180, and a power supply unit 190. It is understood that implementing all of the illustrated components is not a requirement, and that greater or fewer components may alternatively be implemented.

In the example of FIG. 2, the mobile terminal 100 is shown having wireless communication unit 110 configured with several commonly implemented components. For instance, the wireless communication unit 110 typically includes one or more components which permit wireless communication between the mobile terminal 100 and a wireless communication system or network within which the mobile terminal is located.

The wireless communication unit 110 typically includes one or more modules which permit communications such as wireless communications between the mobile terminal 100 and a wireless communication system, communications between the mobile terminal 100 and another mobile terminal, communications between the mobile terminal 100 and an external server. Further, the wireless communication unit 110 typically includes one or more modules which connect the mobile terminal 100 to one or more networks. To facilitate such communications, the wireless communication unit 110 includes one or more of a broadcast receiving module 111, a mobile communication module 112, a wireless Internet module 113, a short-range communication module 114, and a location information module 115.

The input unit 120 includes a camera 121 for obtaining images or video, a microphone 122, which is one type of audio input device for inputting an audio signal, and a user input unit 123 (for example, a touch key, a push key, a mechanical key, a soft key, and the like) for allowing a user to input information. Data (for example, audio, video, image, and the like) is obtained by the input unit 120 and may be analyzed and processed by controller 180 according to device parameters, user commands, and combinations thereof.

The sensing unit 140 is typically implemented using one or more sensors configured to sense internal information of the mobile terminal, the surrounding environment of the mobile terminal, user information, and the like. For example, in FIG. 2, the sensing unit 140 is shown having a proximity sensor 141 and an illumination sensor 142.

If desired, the sensing unit 140 may alternatively or additionally include other types of sensors or devices, such as a touch sensor, an acceleration sensor, a magnetic sensor, a G-sensor, a gyroscope sensor, a motion sensor, an RGB sensor, an infrared (IR) sensor, a finger scan sensor, a ultrasonic sensor, an optical sensor (for example, camera 121), a microphone 122, a battery gauge, an environment sensor (for example, a barometer, a hygrometer, a thermometer, a radiation detection sensor, a thermal sensor, and a gas sensor, among others), and a chemical sensor (for example, an electronic nose, a health care sensor, a biometric sensor, and the like), to name a few. The mobile terminal 100 may be configured to utilize information obtained from sensing unit 140, and in particular, information obtained from one or more sensors of the sensing unit 140, and combinations thereof.

The output unit 150 is typically configured to output various types of information, such as audio, video, tactile output, and the like. The output unit 150 is shown having a display unit 151, an audio output module 152, a haptic module 153, and an optical output module 154.

The display unit 151 may have an inter-layered structure or an integrated structure with a touch sensor in order to facilitate a touch screen. The touch screen may provide an output interface between the mobile terminal 100 and a user, as well as function as the user input unit 123 which provides an input interface between the mobile terminal 100 and the user.

The interface unit 160 serves as an interface with various types of external devices that can be coupled to the mobile terminal 100. The interface unit 160, for example, may include any of wired or wireless ports, external power supply ports, wired or wireless data ports, memory card ports, ports for connecting a device having an identification module, audio input/output (I/O) ports, video I/O ports, earphone ports, and the like. In some cases, the mobile terminal 100 may perform assorted control functions associated with a connected external device, in response to the external device being connected to the interface unit 160.

The memory 170 is typically implemented to store data to support various functions or features of the mobile terminal 100. For instance, the memory 170 may be configured to store application programs executed in the mobile terminal 100, data or instructions for operations of the mobile terminal 100, and the like. Some of these application programs may be downloaded from an external server via wireless communication. Other application programs may be installed within the mobile terminal 100 at time of manufacturing or shipping, which is typically the case for basic functions of the mobile terminal 100 (for example, receiving a call, placing a call, receiving a message, sending a message, and the like). It is common for application programs to be stored in the memory 170, installed in the mobile terminal 100, and executed by the controller 180 to perform an operation (or function) for the mobile terminal 100.

The controller 180 typically functions to control overall operation of the mobile terminal 100, in addition to the operations associated with the application programs. The controller 180 may provide or process information or functions appropriate for a user by processing signals, data, information and the like, which are input or output by the various components depicted in FIG. 2, or activating application programs stored in the memory 170. As one example, the controller 180 controls some or all of the components illustrated in FIGS. 3, 4A, and 4B according to the execution of an application program that have been stored in the memory 170.

The example mobile terminal 100 in FIG. 2 also includes a detecting unit 185 that is configured to detect a biological signal (e.g., a biometric signal) of a user. For example, the biological signal may have been collected using at least one sensor provided in the mobile terminal 100 (e.g., in sensing unit 140). As an example, in some implementations, the mobile terminal 100 may be a wearable device (e.g., a smart watch). The mobile terminal 100 may sense that a user is wearing the mobile terminal 100 and, based on sensing that a user is wearing the mobile terminal 100, the detecting unit 185 may begin detecting the biological signal of the user (e.g., using the sensing unit 140).

The power supply unit 190 can be configured to receive external power or provide internal power in order to supply appropriate power required for operating elements and components included in the mobile terminal 100. The power supply unit 190 may include a battery, and the battery may be configured to be embedded in the terminal body, or configured to be detachable from the terminal body.

Referring still to FIG. 2, various components depicted in this figure will now be described in more detail. Regarding the wireless communication unit 110, the broadcast receiving module 111 is typically configured to receive a broadcast signal and/or broadcast associated information from an external broadcast managing entity via a broadcast channel. The broadcast channel may include a satellite channel, a terrestrial channel, or both. In some implementations, two or more broadcast receiving modules 111 may be utilized to facilitate simultaneously receiving of two or more broadcast channels, or to support switching among broadcast channels.

The broadcast managing entity may be implemented using a server or system which generates and transmits a broadcast signal and/or broadcast associated information, or a server which receives a pre-generated broadcast signal and/or broadcast associated information, and sends such items to the mobile terminal. The broadcast signal may be implemented using any of a TV broadcast signal, a radio broadcast signal, a data broadcast signal, and combinations thereof, among others. The broadcast signal in some cases may further include a data broadcast signal combined with a TV or radio broadcast signal.

The broadcast signal may be encoded according to any of a variety of technical standards or broadcasting methods (for example, International Organization for Standardization (ISO), International Electrotechnical Commission (IEC), Digital Video Broadcast (DVB), Advanced Television Systems Committee (ATSC), and the like) for transmission and reception of digital broadcast signals. The broadcast receiving module 111 can receive the digital broadcast signals using a method appropriate for the transmission method utilized.

Examples of broadcast associated information may include information associated with a broadcast channel, a broadcast program, a broadcast event, a broadcast service provider, or the like. The broadcast associated information may also be provided via a mobile communication network, and in this case, received by the mobile communication module 112.

The broadcast associated information may be implemented in various formats. For instance, broadcast associated information may include an Electronic Program Guide (EPG) of Digital Multimedia Broadcasting (DMB), an Electronic Service Guide (ESG) of Digital Video Broadcast-Handheld (DVB-H), and the like. Broadcast signals and/or broadcast associated information received via the broadcast receiving module 111 may be stored in a suitable device, such as a memory 170.

The mobile communication module 112 can transmit and/or receive wireless signals to and from one or more network entities. Typical examples of a network entity include a base station, an external mobile terminal, a server, and the like. Such network entities form part of a mobile communication network, which is constructed according to technical standards or communication methods for mobile communications (for example, Global System for Mobile Communication (GSM), Code Division Multi Access (CDMA), CDMA2000(Code Division Multi Access 2000), EV-DO (Enhanced Voice-Data Optimized or Enhanced Voice-Data Only), Wideband CDMA (WCDMA), High Speed Downlink Packet access (HSDPA), HSUPA (High Speed Uplink Packet Access), Long Term Evolution (LTE), LTE-A (Long Term Evolution-Advanced), and the like). Examples of wireless signals transmitted and/or received via the mobile communication module 112 include audio call signals, video (telephony) call signals, or various formats of data to support communication of text and multimedia messages.

The wireless Internet module 113 is configured to facilitate wireless Internet access. This module may be internally or externally coupled to the mobile terminal 100. The wireless Internet module 113 may transmit and/or receive wireless signals via communication networks according to wireless Internet technologies.

Examples of such wireless Internet access include Wireless LAN (WLAN), Wireless Fidelity (Wi-Fi), Wi-Fi Direct, Digital Living Network Alliance (DLNA), Wireless Broadband (WiBro), Worldwide Interoperability for Microwave Access (WiMAX), High Speed Downlink Packet Access (HSDPA), HSUPA (High Speed Uplink Packet Access), Long Term Evolution (LTE), LTE-A (Long Term Evolution-Advanced), and the like. The wireless Internet module 113 may transmit/receive data according to one or more of such wireless Internet technologies, and other Internet technologies as well.

In some implementations, when the wireless Internet access is implemented according to, for example, WiBro, HSDPA, HSUPA, GSM, CDMA, WCDMA, LTE, LTE-A and the like, as part of a mobile communication network, the wireless Internet module 113 performs such wireless Internet access. As such, the Internet module 113 may cooperate with, or function as, the mobile communication module 112.

The short-range communication module 114 is configured to facilitate short-range communications. Suitable technologies for implementing such short-range communications include BLUETOOTH™, Radio Frequency IDentification (RFID), Infrared Data Association (IrDA), Ultra-WideBand (UWB), ZigBee, Near Field Communication (NFC), Wireless-Fidelity (Wi-Fi), Wi-Fi Direct, Wireless USB (Wireless Universal Serial Bus), and the like. The short-range communication module 114 in general supports wireless communications between the mobile terminal 100 and a wireless communication system, communications between the mobile terminal 100 and another mobile terminal 100, or communications between the mobile terminal and a network where another mobile terminal 100 (or an external server) is located, via wireless area networks. One example of the wireless area networks is a wireless personal area networks.

In some implementations, another mobile terminal (which may be configured similarly to mobile terminal 100) may be a wearable device, for example, a smart watch, a smart glass or a head mounted display (HMD), which is able to exchange data with the mobile terminal 100 (or otherwise cooperate with the mobile terminal 100). The short-range communication module 114 may sense or recognize the wearable device, and permit communication between the wearable device and the mobile terminal 100. In addition, when the sensed wearable device is a device which is authenticated to communicate with the mobile terminal 100, the controller 180, for example, may cause transmission of data processed in the mobile terminal 100 to the wearable device via the short-range communication module 114. Hence, a user of the wearable device may use the data processed in the mobile terminal 100 on the wearable device. For example, when a call is received in the mobile terminal 100, the user may answer the call using the wearable device. Also, when a message is received in the mobile terminal 100, the user can check the received message using the wearable device.

The location information module 115 is generally configured to detect, calculate, derive or otherwise identify a position of the mobile terminal. As an example, the location information module 115 includes a Global Position System (GPS) module, a Wi-Fi module, or both. If desired, the location information module 115 may alternatively or additionally function with any of the other modules of the wireless communication unit 110 to obtain data related to the position of the mobile terminal.

As one example, when the mobile terminal uses a GPS module, a position of the mobile terminal may be acquired using a signal sent from a GPS satellite. As another example, when the mobile terminal uses the Wi-Fi module, a position of the mobile terminal can be acquired based on information related to a wireless access point (AP) which transmits or receives a wireless signal to or from the Wi-Fi module.

The input unit 120 may be configured to permit various types of input to the mobile terminal 100. Examples of such input include audio, image, video, data, and user input. Image and video input is often obtained using one or more cameras 121. Such cameras 121 may process image frames of still pictures or video obtained by image sensors in a video or image capture mode. The processed image frames can be displayed on the display unit 151 or stored in memory 170. In some cases, the cameras 121 may be arranged in a matrix configuration to permit a plurality of images having various angles or focal points to be input to the mobile terminal 100. As another example, the cameras 121 may be located in a stereoscopic arrangement to acquire left and right images for implementing a stereoscopic image.

The microphone 122 is generally implemented to permit audio input to the mobile terminal 100. The audio input can be processed in various manners according to a function being executed in the mobile terminal 100. If desired, the microphone 122 may include assorted noise removing algorithms to remove unwanted noise generated in the course of receiving the external audio.

The user input unit 123 is a component that permits input by a user. Such user input may enable the controller 180 to control operation of the mobile terminal 100. The user input unit 123 may include one or more of a mechanical input element (for example, a key, a button located on a front and/or rear surface or a side surface of the mobile terminal 100, a dome switch, a jog wheel, a jog switch, and the like), or a touch-sensitive input, among others. As one example, the touch-sensitive input may be a virtual key or a soft key, which is displayed on a touch screen through software processing, or a touch key which is located on the mobile terminal at a location that is other than the touch screen. On the other hand, the virtual key or the visual key may be displayed on the touch screen in various shapes, for example, graphic, text, icon, video, or a combination thereof.

The sensing unit 140 is generally configured to sense one or more of internal information of the mobile terminal, surrounding environment information of the mobile terminal, user information, or the like. The controller 180 generally cooperates with the sending unit 140 to control operation of the mobile terminal 100 or execute data processing, a function or an operation associated with an application program installed in the mobile terminal based on the sensing provided by the sensing unit 140. The sensing unit 140 may be implemented using any of a variety of sensors, some of which will now be described in more detail.

The proximity sensor 141 may include a sensor to sense presence or absence of an object approaching a surface, or an object located near a surface, by using an electromagnetic field, infrared rays, or the like without a mechanical contact. The proximity sensor 141 may be arranged at an inner region of the mobile terminal covered by the touch screen, or near the touch screen.

The proximity sensor 141, for example, may include any of a transmissive type photoelectric sensor, a direct reflective type photoelectric sensor, a mirror reflective type photoelectric sensor, a high-frequency oscillation proximity sensor, a capacitance type proximity sensor, a magnetic type proximity sensor, an infrared rays proximity sensor, and the like. When the touch screen is implemented as a capacitance type, the proximity sensor 141 can sense proximity of a pointer relative to the touch screen by changes of an electromagnetic field, which is responsive to an approach of an object with conductivity. In this case, the touch screen (touch sensor) may also be categorized as a proximity sensor.

The term "proximity touch" will often be referred to herein to denote the scenario in which a pointer is positioned to be proximate to the touch screen without contacting the touch screen. The term "contact touch" will often be referred to herein to denote the scenario in which a pointer makes physical contact with the touch screen. For the position corresponding to the proximity touch of the pointer relative to the touch screen, such position will correspond to a position where the pointer is perpendicular to the touch screen. The proximity sensor 141 may sense proximity touch, and proximity touch patterns (for example, distance, direction, speed, time, position, moving status, and the like).

In general, controller 180 processes data corresponding to proximity touches and proximity touch patterns sensed by the proximity sensor 141, and cause output of visual information on the touch screen. In addition, the controller 180 can control the mobile terminal 100 to execute different operations or process different data according to whether a touch with respect to a point on the touch screen is either a proximity touch or a contact touch.

A touch sensor can sense a touch applied to the touch screen, such as display unit 151, using any of a variety of touch methods. Examples of such touch methods include a resistive type, a capacitive type, an infrared type, and a magnetic field type, among others.

As one example, the touch sensor may be configured to convert changes of pressure applied to a specific part of the display unit 151, or convert capacitance occurring at a specific part of the display unit 151, into electric input signals. The touch sensor may also be configured to sense not only a touched position and a touched area, but also touch pressure and/or touch capacitance. A touch object is generally used to apply a touch input to the touch sensor. Examples of typical touch objects include a finger, a touch pen, a stylus pen, a pointer, or the like.

When a touch input is sensed by a touch sensor, corresponding signals may be transmitted to a touch controller. The touch controller may process the received signals, and then transmit corresponding data to the controller 180. Accordingly, the controller 180 may sense which region of the display unit 151 has been touched. Here, the touch controller may be a component separate from the controller 180, the controller 180, and combinations thereof.

In some implementations, the controller 180 may execute the same or different controls according to a type of touch object that touches the touch screen or a touch key provided in addition to the touch screen. Whether to execute the same or different control according to the object which provides a touch input may be decided based on a current operating state of the mobile terminal 100 or a currently executed application program, for example.

The touch sensor and the proximity sensor may be implemented individually, or in combination, to sense various types of touches. Such touches includes a short (or tap) touch, a long touch, a multi-touch, a drag touch, a flick touch, a pinch-in touch, a pinch-out touch, a swipe touch, a hovering touch, and the like.

If desired, an ultrasonic sensor may be implemented to recognize position information relating to a touch object using ultrasonic waves. The controller 180, for example, may calculate a position of a wave generation source based on information sensed by an illumination sensor and a plurality of ultrasonic sensors. Since light is much faster than ultrasonic waves, the time for which the light reaches the optical sensor is much shorter than the time for which the ultrasonic wave reaches the ultrasonic sensor. The position of the wave generation source may be calculated using this fact. For instance, the position of the wave generation source may be calculated using the time difference from the time that the ultrasonic wave reaches the sensor based on the light as a reference signal.

The camera 121 typically includes at least one a camera sensor (CCD, CMOS etc.), a photo sensor (or image sensors), and a laser sensor.

Implementing the camera 121 with a laser sensor may allow detection of a touch of a physical object with respect to a 3D stereoscopic image. The photo sensor may be laminated on, or overlapped with, the display device. The photo sensor may be configured to scan movement of the physical object in proximity to the touch screen. In more detail, the photo sensor may include photo diodes and transistors at rows and columns to scan content received at the photo sensor using an electrical signal which changes according to the quantity of applied light. Namely, the photo sensor may calculate the coordinates of the physical object according to variation of light to thus obtain position information of the physical object.

The display unit 151 is generally configured to output information processed in the mobile terminal 100. For example, the display unit 151 may display execution screen information of an application program executing at the mobile terminal 100 or user interface (UI) and graphic user interface (GUI) information in response to the execution screen information.

In some implementations, the display unit 151 may be implemented as a stereoscopic display unit for displaying stereoscopic images.

A typical stereoscopic display unit may employ a stereoscopic display scheme such as a stereoscopic scheme (a glass scheme), an auto-stereoscopic scheme (glassless scheme), a projection scheme (holographic scheme), or the like.

The audio output module 152 is generally configured to output audio data. Such audio data may be obtained from any of a number of different sources, such that the audio data may be received from the wireless communication unit 110 or may have been stored in the memory 170. The audio data may be output during modes such as a signal reception mode, a call mode, a record mode, a voice recognition mode, a broadcast reception mode, and the like. The audio output module 152 can provide audible output related to a particular function (e.g., a call signal reception sound, a message reception sound, etc.) performed by the mobile terminal 100. The audio output module 152 may also be implemented as a receiver, a speaker, a buzzer, or the like.

A haptic module 153 can be configured to generate various tactile effects that a user feels, perceive, or otherwise experience. A typical example of a tactile effect generated by the haptic module 153 is vibration. The strength, pattern and the like of the vibration generated by the haptic module 153 can be controlled by user selection or setting by the controller. For example, the haptic module 153 may output different vibrations in a combining manner or a sequential manner.

Besides vibration, the haptic module 153 can generate various other tactile effects, including an effect by stimulation such as a pin arrangement vertically moving to contact skin, a spray force or suction force of air through a jet orifice or a suction opening, a touch to the skin, a contact of an electrode, electrostatic force, an effect by reproducing the sense of cold and warmth using an element that can absorb or generate heat, and the like.

The haptic module 153 can also be implemented to allow the user to feel a tactile effect through a muscle sensation such as the user's fingers or arm, as well as transferring the tactile effect through direct contact. Two or more haptic modules 153 may be provided according to the particular configuration of the mobile terminal 100.

An optical output module 154 can output a signal for indicating an event generation using light of a light source. Examples of events generated in the mobile terminal 100 may include message reception, call signal reception, a missed call, an alarm, a schedule notice, an email reception, information reception through an application, and the like.

A signal output by the optical output module 154 may be implemented in such a manner that the mobile terminal emits monochromatic light or light with a plurality of colors. The signal output may be terminated as the mobile terminal senses that a user has checked the generated event, for example.

The interface unit 160 serves as an interface for external devices to be connected with the mobile terminal 100. For example, the interface unit 160 can receive data transmitted from an external device, receive power to transfer to elements and components within the mobile terminal 100, or transmit internal data of the mobile terminal 100 to such external device. The interface unit 160 may include wired or wireless headset ports, external power supply ports, wired or wireless data ports, memory card ports, ports for connecting a device having an identification module, audio input/output (I/O) ports, video I/O ports, earphone ports, or the like.

The identification module may be a chip that stores various types of information for authenticating authority of using the mobile terminal 100 and may include a user identity module (UIM), a subscriber identity module (SIM), a universal subscriber identity module (USIM), and the like. In addition, the device having the identification module (also referred to herein as an "identifying device") may take the form of a smart card. Accordingly, the identifying device can be connected with the terminal 100 via the interface unit 160.

When the mobile terminal 100 is connected with an external cradle, the interface unit 160 can serve as a passage to allow power from the cradle to be supplied to the mobile terminal 100 or may serve as a passage to allow various command signals input by the user from the cradle to be transferred to the mobile terminal there through. Various command signals or power input from the cradle may operate as signals for recognizing that the mobile terminal is properly mounted on the cradle.

The memory 170 can store programs to support operations of the controller 180 and store input/output data (for example, phonebook, messages, still images, videos, etc.). The memory 170 may store data related to various patterns of vibrations and audio which are output in response to touch inputs on the touch screen.

The memory 170 may include one or more types of storage mediums including a Flash memory, a hard disk, a solid state disk, a silicon disk, a multimedia card micro type, a card-type memory (e.g., SD or DX memory, etc.), a Random Access Memory (RAM), a Static Random Access Memory (SRAM), a Read-Only Memory (ROM), an Electrically Erasable Programmable Read-Only Memory (EE-PROM), a Programmable Read-Only memory (PROM), a magnetic memory, a magnetic disk, an optical disk, and the like. The mobile terminal 100 may also be operated in relation to a network storage device that performs the storage function of the memory 170 over a network, such as the Internet.

The controller 180 may typically control the general operations of the mobile terminal 100. For example, the controller 180 may set or release a lock state for restricting a user from inputting a control command with respect to applications when a status of the mobile terminal meets a preset condition.

The controller 180 can also perform the controlling and processing associated with voice calls, data communications, video calls, and the like, or perform pattern recognition processing to recognize a handwriting input or a picture drawing input performed on the touch screen as characters or images, respectively. In addition, the controller 180 can control one or a combination of those components in order to implement various exemplary implementations disclosed herein.

The power supply unit 190 receives external power or provides internal power and supply the appropriate power required for operating respective elements and components included in the mobile terminal 100. The power supply unit 190 may include a battery, which is typically rechargeable or be detachably coupled to the terminal body for charging.

The power supply unit 190 may include a connection port. The connection port may be configured as one example of the interface unit 160 to which an external charger for supplying power to recharge the battery is electrically connected.

As another example, the power supply unit 190 may be configured to recharge the battery in a wireless manner without use of the connection port. In this example, the power supply unit 190 can receive power, transferred from an external wireless power transmitter, using at least one of an inductive coupling method which is based on magnetic induction or a magnetic resonance coupling method which is based on electromagnetic resonance.

In some implementations, the mobile terminal 100 may be connected to an external device (e.g., another mobile terminal 100) such that the mobile terminal 100 perform communication with the external device wirelessly. For example, the wireless communication may be any one of mobile communication, wireless Internet communication, and near field communication. As a specific example, if the wireless communication is a near field communication, the near field communication may be any one of Bluetooth communication, radio frequency identification (RFID), Wi-Fi communication, infrared data association (IrDA), ultra wide band (UWB) communication, or ZigBee communication.

Hereinafter, it is assumed that the wireless communication is Bluetooth communication or Wi-Fi communication. However, the present disclosure is not limited thereto and the external device may be any electronic device capable of performing Bluetooth communication or Wi-Fi communication. For example, the external device may be Bluetooth headset, another mobile terminal of a counterpart, a printer, and the like (not limited thereto).

In some implementations, the external device may include components identical to or similar to those of the mobile terminal 100 in FIG. 2. For example, the external device may include a wireless communication unit (e.g., wireless communication unit 110 in FIG. 2), a signal modulation and demodulation unit, an output unit (e.g., output unit 150 in FIG. 2) such as, for example, a speaker, and an input unit (e.g., input unit 120 in FIG. 2) such as, for example, a microphone.

As a specific example, in the external device, the wireless communication unit (e.g., wireless communication unit 110) may allow the external device to communicate (e.g., via near field communication) with the mobile terminal 100 according to a corresponding communication standard. Also, the signal modulation and demodulation unit may demodulate a signal received from the mobile terminal 100 through wireless communication or modulate a signal to be transmitted to the mobile terminal 100. Also, the output unit (e.g., output unit 150) may output audio corresponding to the demodulated signal, and the input unit (e.g., input unit 120) may receive audio from the user.

Various implementations described herein may be implemented in a computer-readable medium, a machine-readable medium, or similar medium using, for example, software, hardware, or any combination thereof.

In some implementations, the mobile terminal 100 of FIG. 2 may be configured as a device which is wearable on a human body. Examples of the wearable device include a smart watch, a smart glass, a head mounted display (HMD), and the like. In some implementations, the wearable device may cooperate with another device (e.g., a smart phone), or the mobile terminal itself may include both a wearable device and another device (e.g., a smart phone). As such, a mobile terminal may include one or more devices, some of which may be wearable devices.

In some implementations, the mobile terminal 100 may include a wearable device that is implemented separately from another mobile device (e.g., a smart phone), and the wearable device can exchange data with (or cooperate with) the other mobile device (e.g., a smart phone). In such implementations, the wearable device may have functionality that is less than the cooperating mobile device. For instance, the short-range communication module 114 of a mobile device may sense or recognize a wearable device that is near-enough to communicate with the mobile device. In addition, when the sensed wearable device is a device which is authenticated to communicate with the mobile device, the controller 180 may transmit data processed in the mobile device to the wearable device via the short-range communication module 114, for example. Hence, a user of the wearable device can use the data processed in the mobile device on the wearable device. For example, when a call is received in the mobile device, the user can answer the call using the wearable device. Also, when a message is received in the mobile device, the user can check the received message using the wearable device.

Figure 3:
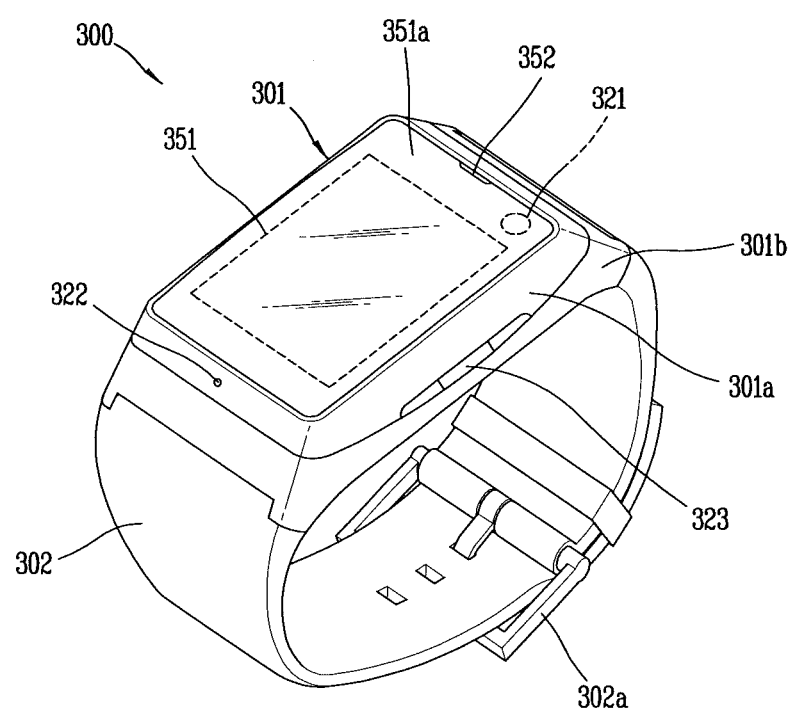
FIG. 3 is a schematic diagram illustrating an example of a watch-type mobile terminal.

FIG. 3 is a perspective view illustrating one example of a watch-type implementation of a wearable device. In some implementations, the watch-type device 300 of FIG. 3 may itself implement the functionality of the mobile terminal 100 of FIG. 2. In some implementations, the watch-type device 300 of FIG. 3 may wirelessly communicate and cooperate with another mobile device (e.g., a smart phone) to collectively implement the functionality of the mobile terminal 100 of FIG. 2. As illustrated in FIG. 3, the watch-type wearable device 300 includes a main body 301 with a display unit 351 and a band 302 connected to the main body 301 so as to be wearable on a user wrist. In general, the wearable device 300 may be configured to include features that are the same or similar to those of the mobile terminal 100 of FIG. 2.

The main body 301 may include a case having a certain appearance. As illustrated, the case may include a first case 301a and a second case 301b cooperatively defining an inner space for accommodating various electronic components. Other configurations are possible. For instance, a single case may alternatively be implemented, with such a case being configured to define the inner space, thereby implementing a mobile terminal 300 with a uni-body.

The watch-type device 300 can perform wireless communication, and an antenna for the wireless communication can be installed in the main body 301. The antenna may extend its function using the case. For example, a case including a conductive material may be electrically connected to the antenna to extend a ground area or a radiation area.

The display unit 351 is shown located at the front side of the main body 301 so that displayed information is viewable to a user. In some implementations, the display unit 351 includes a touch sensor so that the display unit can function as a touch screen. As illustrated, window 351a is positioned on the first case 301a to form a front surface of the terminal body together with the first case 301a.

The illustrated example includes audio output module 352, a camera 321, a microphone 322, and a user input unit 323 positioned on the main body 301. When the display unit 351 is implemented as a touch screen, additional function keys may be minimized or eliminated. For example, when the touch screen is implemented, the user input unit 323 may be omitted.

The band 302 is commonly worn on the user's wrist and may be made of a flexible material for facilitating wearing of the device. As one example, the band 302 may be made of fur, rubber, silicon, synthetic resin, or the like. The band 302 may also be configured to be detachable from the main body 301. Accordingly, the band 302 may be replaceable with various types of bands according to a user's preference.

In one configuration, the band 302 may be used for extending the performance of the antenna. For example, the band may include therein a ground extending portion (not shown) electrically connected to the antenna to extend a ground area.

The band 302 may include fastener 302a. The fastener 302a may be implemented into a buckle type, a snap-fit hook structure, a Velcro® type, or the like, and include a flexible section or material. The drawing illustrates an example that the fastener 302a is implemented using a buckle.

In some implementations, the smart watch 300 in FIG. 3 may communicate with an external device (e.g., a smart phone). For example, in some implementations, the smart watch 300 may have less functionality than the mobile terminal 100 in FIG. 2, and may cooperate with an external device (e.g., a smart phone) to collectively perform the functions of the mobile terminal 100 of FIG. 2.

Figure 4A:
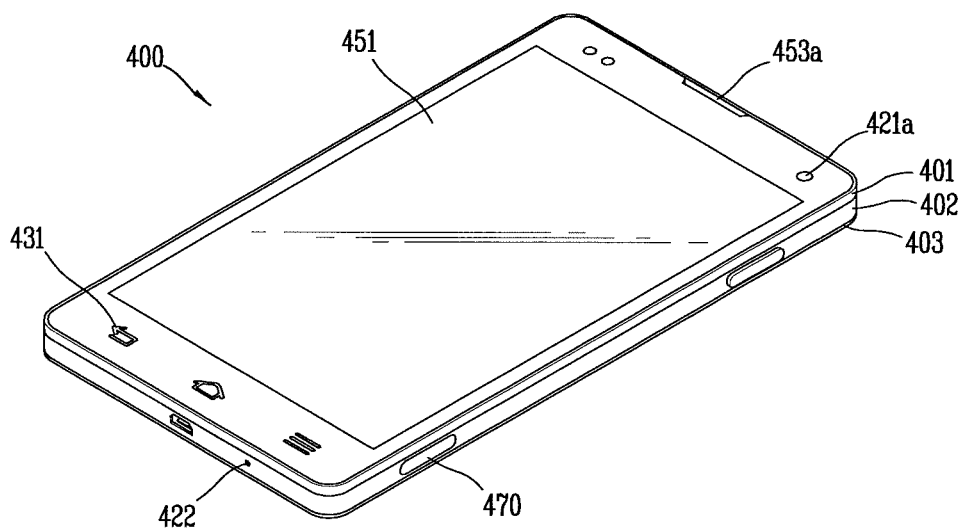
FIGS. 4A and 4B are schematic diagrams illustrating examples of a bar-type mobile terminal.
Figure 4B:
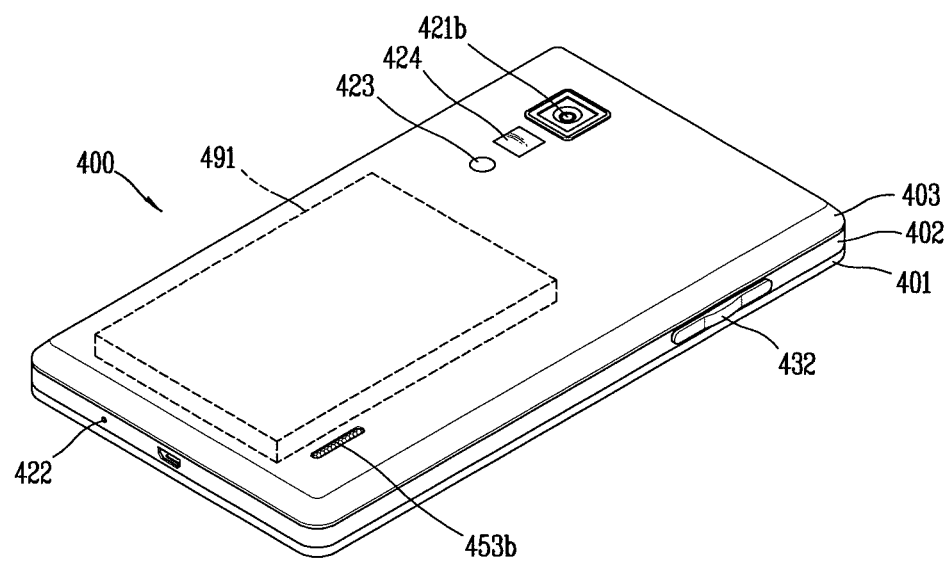

Referring now to FIGS. 4A and 4B, a mobile terminal is described with reference to a bar-type terminal body. For example, the bar-type mobile terminal 400 of FIGS. 4A and 4B may communicate and cooperate with another device, such as a wearable device (e.g., wearable device 300 in FIG. 3). However, the bar-type mobile terminal 400 in FIGS. 4A and 4B is just one example of a mobile terminal, and in general, the mobile terminal 100 of FIG. 2 may be implemented in any of a variety of different configurations. Examples of such configurations include watch-type (e.g., the wearable device 300 in FIG. 3), clip-type, glasses-type, or as a folder-type, flip-type, slide-type, swing-type, and swivel-type in which two and more bodies are combined with each other in a relatively movable manner, and combinations thereof. Discussion herein will often relate to a particular type of mobile terminal (for example, bar-type, watch-type, glasses-type, and the like). However, such teachings with regard to a particular type of mobile terminal will generally apply to other types of mobile terminals as well.

The example bar-type mobile terminal 400 in FIG. 4A includes a case (for example, frame, housing, cover, and the like) forming the appearance of the terminal. In this implementation, the case is formed using a front case 401 and a rear case 402. Various electronic components are incorporated into a space formed between the front case 401 and the rear case 402. At least one middle case may be additionally positioned between the front case 401 and the rear case 402.

The display unit 451 is shown located on the front side of the terminal body to output information. As illustrated, a window 451a of the display unit 451 may be mounted to the front case 401 to form the front surface of the terminal body together with the front case 401.

In some implementations, electronic components may also be mounted to the rear case 402. Examples of such electronic components include a detachable battery 491, an identification module, a memory card, and the like. Rear cover 403 is shown covering the electronic components, and this cover may be detachably coupled to the rear case 402. Therefore, when the rear cover 403 is detached from the rear case 402, the electronic components mounted to the rear case 402 are externally exposed.

As illustrated, when the rear cover 403 is coupled to the rear case 402, a side surface of the rear case 402 is partially exposed. In some cases, upon the coupling, the rear case 402 may also be completely shielded by the rear cover 403. In some implementations, the rear cover 403 may include an opening for externally exposing a camera 421b or an audio output module 452b.

The cases 401, 402, 403 may be formed by injection-molding synthetic resin or may be formed of a metal, for example, stainless steel (STS), aluminum (Al), titanium (Ti), or the like.

As an alternative to the example in which the plurality of cases form an inner space for accommodating components, the bar-type mobile terminal 400 of FIG. 4A may be configured such that one case forms the inner space. In this example, a bar-type mobile terminal 400 having a uni-body is formed in such a manner that synthetic resin or metal extends from a side surface to a rear surface.

In some implementations, the bar-type mobile terminal 400 may include a waterproofing unit (not shown) for preventing introduction of water into the terminal body. For example, the waterproofing unit may include a waterproofing member which is located between the window 451a and the front case 401, between the front case 401 and the rear case 402, or between the rear case 402 and the rear cover 403, to hermetically seal an inner space when those cases are coupled.

The bar-type mobile terminal 400 in FIG. 4A may include the display unit 451, first and second audio output units 452a and 452b, the proximity sensor 441, an illumination sensor 442, an optical output module 454, first and second cameras 421a and 421b, first and second manipulation units 423a and 423b, a microphone 422, an interface unit 460, and the like.

Hereinafter, as illustrated in FIGS. 4A and 4B, the example bar-type mobile terminal 400 in which the display unit 451, the first audio output unit 452a, the proximity sensor 441, the illumination sensor 442, the optical output module 454, the first camera 421a, and the first manipulation unit 423a are disposed on a front surface of the terminal body, the second manipulation unit 423b, the microphone 422, and the interface unit 460 are disposed on the side of the terminal body, and the second audio output unit 452b and the second camera 421b are disposed on a rear surface of the terminal body will be described as an example.

However, the components are not limited to the configuration. The components may be excluded, replaced, or disposed on other surfaces as needed. For example, the first manipulation unit 423a may not be provided on the front surface of the terminal body, and the second audio output unit 452b may be provided on the side of the terminal body, rather than on the rear surface of the terminal body.

The display unit 451 may display (or output) information processed in the bar-type mobile terminal 400. For example, the display unit 451 may display executed screen information of an application program driven in the mobile terminal 400, or user interface (UI) information or graphic user interface (GUI) information according to the executed screen information.

The display unit 451 may include a liquid crystal display (LCD), a thin film transistor-liquid crystal display (TFT-LCD), an organic light emitting diode (OLED), a flexible display, a 3-dimensional (3D) display, and an e-ink display.

The display unit 451 may be implemented using two display devices, which can implement the same or different display technology. For instance, a plurality of the display units 451 may be arranged on one side, either spaced apart from each other, or these devices may be integrated, or these devices may be arranged on different surfaces.

The display unit 451 may also include a touch sensor which senses a touch input received at the display unit. When a touch is input to the display unit 451, the touch sensor may be configured to sense this touch and the controller 480, for example, may generate a control command or other signal corresponding to the touch. The content which is input in the touching manner may be a text or numerical value, or a menu item which can be indicated or designated in various modes.

The touch sensor may be configured in a form of a film having a touch pattern, disposed between the window 451a and a display on a rear surface of the window 451a, or a metal wire which is patterned directly on the rear surface of the window 451a. Alternatively, the touch sensor may be integrally formed with the display. For example, the touch sensor may be disposed on a substrate of the display or within the display.

The display unit 451 may also form a touch screen together with the touch sensor. Here, the touch screen may serve as the user input unit 423 (e.g., user input unit 123 in FIG. 2). Therefore, the touch screen may replace at least some of the functions of the first manipulation unit 423a.

The first audio output module 452a may be implemented in the form of a speaker to output voice audio, alarm sounds, multimedia audio reproduction, and the like.

The window 451a of the display unit 451 will typically include an aperture to permit audio generated by the first audio output module 452a to pass. One alternative is to allow audio to be released along an assembly gap between the structural bodies (for example, a gap between the window 451a and the front case 401). In this case, a hole independently formed to output audio sounds may not be seen or is otherwise hidden in terms of appearance, thereby further simplifying the appearance and manufacturing of the bar-type mobile terminal 400.

The optical output module 454 can be configured to output light for indicating an event generation. Examples of such events include a message reception, a call signal reception, a missed call, an alarm, a schedule notice, an email reception, information reception through an application, and the like. When a user has checked a generated event, the controller can control the optical output unit 454 to stop the light output.

The first camera 421a can process image frames such as still or moving images obtained by the image sensor in a capture mode or a video call mode. The processed image frames can then be displayed on the display unit 451 or stored in the memory 470.

The first and second manipulation units 423a and 423b are examples of the user input unit 423, which may be manipulated by a user to provide input to the bar-type mobile terminal 400. The first and second manipulation units 423a and 423b may also be commonly referred to as a manipulating portion, and may employ any tactile method that allows the user to perform manipulation such as touch, push, scroll, or the like. The first and second manipulation units 423a and 423b may also employ any non-tactile method that allows the user to perform manipulation such as proximity touch, hovering, or the like.

FIG. 4A illustrates the first manipulation unit 423a as a touch key, but possible alternatives include a mechanical key, a push key, a touch key, and combinations thereof.

Input received at the first and second manipulation units 423a and 423b may be used in various ways. For example, the first manipulation unit 423a may be used by the user to provide an input to a menu, home key, cancel, search, or the like, and the second manipulation unit 423b may be used by the user to provide an input to control a volume level being output from the first or second audio output modules 452a or 452b, to switch to a touch recognition mode of the display unit 451, or the like.

As another example of the user input unit 423, a rear input unit (not shown) may be located on the rear surface of the terminal body. The rear input unit can be manipulated by a user to provide input to the bar-type mobile terminal 400. The input may be used in a variety of different ways. For example, the rear input unit may be used by the user to provide an input for power on/off, start, end, scroll, control volume level being output from the first or second audio output modules 452a or 452b, switch to a touch recognition mode of the display unit 451, and the like. The rear input unit may be configured to permit touch input, a push input, or combinations thereof.

The rear input unit may be located to overlap the display unit 451 of the front side in a thickness direction of the terminal body. As one example, the rear input unit may be located on an upper end portion of the rear side of the terminal body such that a user can easily manipulate it using a forefinger when the user grabs the terminal body with one hand. However, the present disclosure is not limited thereto and a position of the rear input unit may be modified.

When the rear input unit is provided on the rear surface of the terminal body, a new user interface may be implemented. Also, when the touch screen or the rear input unit as described above replaces at least some functions of the first manipulation unit 423a provided on the front surface of the terminal body so the first manipulation unit 423a is omitted from the front surface of the terminal body, the display unit 451 can have a larger screen.

As a further alternative, the bar-type mobile terminal 400 may include a finger scan sensor which scans a user's fingerprint. The controller 480 can then use fingerprint information sensed by the finger scan sensor as part of an authentication procedure. The finger scan sensor may also be installed in the display unit 451 or implemented in the user input unit 423.

The microphone 422 is shown located at an end of the mobile terminal 400, but other locations are possible. If desired, multiple microphones may be implemented, with such an arrangement permitting the receiving of stereo sounds.

The interface unit 460 may serve as a path allowing the mobile terminal 400 to interface with external devices. For example, the interface unit 460 may include one or more of a connection terminal for connecting to another device (for example, an earphone, an external speaker, or the like), a port for near field communication (for example, an Infrared Data Association (IrDA) port, a Bluetooth port, a wireless LAN port, and the like), or a power supply terminal for supplying power to the bar-type mobile terminal 400. The interface unit 460 may be implemented in the form of a socket for accommodating an external card, such as Subscriber Identification Module (SIM), User Identity Module (UIM), or a memory card for information storage.

The second camera 421b is shown located at the rear side of the terminal body and includes an image capturing direction that is substantially opposite to the image capturing direction of the first camera unit 421a.

The second camera 421b can include a plurality of lenses arranged along at least one line. The plurality of lenses may also be arranged in a matrix configuration. The cameras may be referred to as an "array camera." When the second camera 421b is implemented as an array camera, images may be captured in various manners using the plurality of lenses and images with better qualities.

As shown in FIG. 4B, a flash 424 is shown adjacent to the second camera 421b. When an image of a subject is captured with the camera 421b, the flash 424 may illuminate the subject.

As shown in FIG. 4A, the second audio output module 452b can be located on the terminal body. The second audio output module 452b may implement stereophonic sound functions in conjunction with the first audio output module 452a, and may be also used for implementing a speaker phone mode for call communication.

At least one antenna for wireless communication may be located on the terminal body. The antenna may be installed in the terminal body or formed by the case. For example, an antenna which configures a part of the broadcast receiving module 411 may be retractable into the terminal body. Alternatively, an antenna may be formed using a film attached to an inner surface of the rear cover 403, or a case that includes a conductive material.

A power supply unit 490 for supplying power to the bar-type mobile terminal 400 may include a battery 491, which is mounted in the terminal body or detachably coupled to an outside of the terminal body.

The battery 491 may receive power via a power source cable connected to the interface unit 460. Also, the battery 491 can be recharged in a wireless manner using a wireless charger. Wireless charging may be implemented by magnetic induction or electromagnetic resonance.

The rear cover 403 is shown coupled to the rear case 402 for shielding the battery 491, to prevent separation of the battery 491, and to protect the battery 491 from an external impact or from foreign material. When the battery 491 is detachable from the terminal body, the rear case 403 may be detachably coupled to the rear case 402.

An accessory for protecting an appearance or assisting or extending the functions of the bar-type mobile terminal 400 can also be provided on the bar-type mobile terminal 400. As one example of an accessory, a cover or pouch for covering or accommodating at least one surface of the bar-type mobile terminal 400 may be provided. The cover or pouch may cooperate with the display unit 451 to extend the function of the bar-type mobile terminal 400. Another example of the accessory is a touch pen for assisting or extending a touch input to a touch screen.

The mobile terminal 100 according to some implementations of the present disclosure including at least one of the components as described above may be connected to an e-Call system of a vehicle to receive information related to a state of the vehicle. Also, when an accident event of the vehicle is sensed based on the received information, a biological signal of a wearer is detected and analyzed to obtain state information of the wearer. In some implementations, the state information of the wearer may be classified in discrete levels, or stages. Thereafter, when a predetermined condition is met, the mobile terminal 100 interwork with the connected e-Call system to transmit the state information of the wearer and the information related to the state of the vehicle to a predetermined call center to request for rescue.

Figure 5:
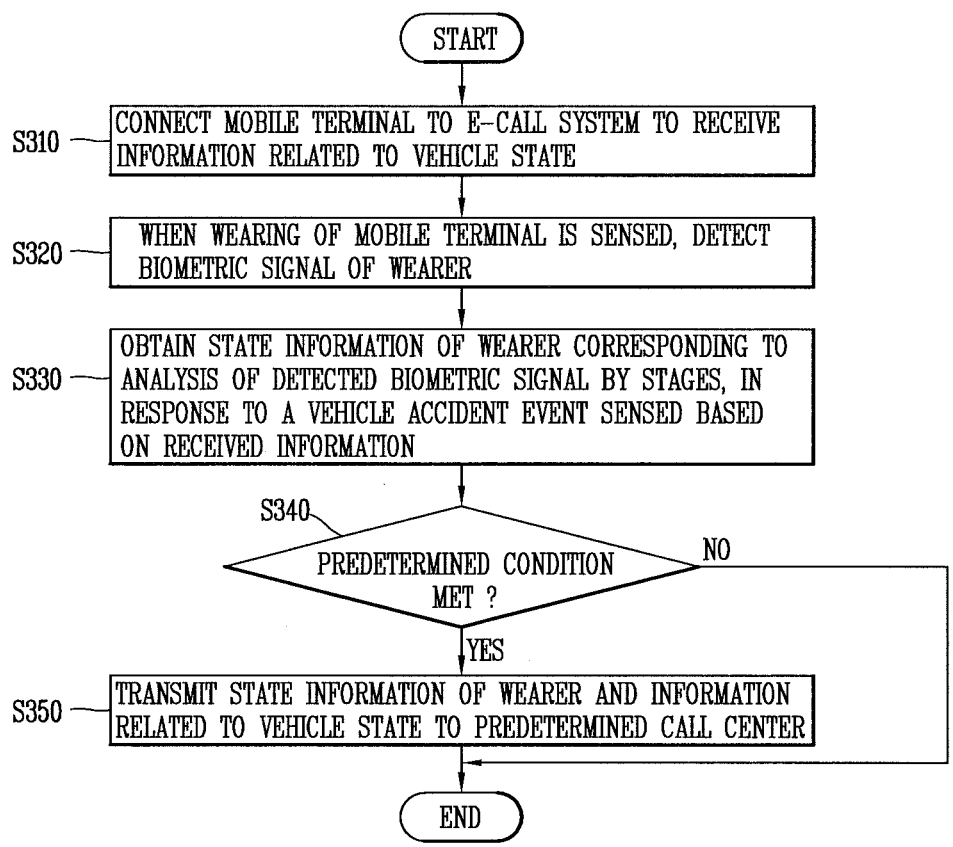
FIGS. 5 through 8 are flow charts illustrating examples of operating a system that includes a mobile terminal.

FIG. 5 is a flow chart illustrating an example of a method for dealing with (or handling) an accident of a vehicle using a watch-type mobile terminal (e.g., watch-type mobile terminal 100 in FIGS. 1 and 300 in FIG. 3).

First, the watch-type mobile terminal is connected to an external system (e.g., e-Call system 20 in FIG. 1) and receives information related to a state of a vehicle (S310).

As mentioned above, an e-Call system of a vehicle may be an emergency call system for transmitting information required for rescue such as a current location, state, or the like, of a vehicle to an emergency rescue agency when an emergency, such as a car accident, or the like, occurs. The e-Call system may be implemented, for example, through a telematics device installed in a vehicle.

In some implementations, information related to a state of a vehicle may include additional signals related to other operations of the vehicle, such as an operation of an airbag device, an operation of an impact sensor of a vehicle, or the like, as well as location information of a vehicle using a GPS, whether a vehicle is running, a set destination, and a traveling route.

The watch-type mobile terminal may be connected to the e-Call system of a vehicle through a manual command (e.g., a predetermined input) from a user, or automatically without necessarily requiring a command from a user. For example, in some implementations, when a predetermined input applied to a display unit (e.g., display unit 351 in FIG. 3) of the watch-type mobile terminal is sensed, the watch-type mobile terminal may be connected to the e-Call system. As another example, in some implementations, when a driver who wears the watch-type mobile terminal enters a vehicle, the watch-type mobile terminal may be automatically connected to the e-Call system of the vehicle.

In some implementations, the connection between the watch-type mobile terminal and the e-Call system may be performed using a suitable wireless or wired communications technique such as, for example, a near-field communication standard such as Bluetooth, or the like, a wireless Internet standard such as Wi-Fi, or the like, an external device interface standard such as a universal serial bus (USB), or the like.

After the mobile terminal connects to the e-Call system, the watch-type mobile terminal detects that a user is wearing the terminal body of the mobile terminal, and the watch-type mobile terminal detects a biological signal of the wearer (step S320).

The wearer of the terminal body may refer to a driver or a passenger who enters a vehicle. The wearing of the mobile terminal generally refers to the terminal body of the mobile terminal coming into contact with a portion of the user's body. For example, in some implementations, this may include the terminal body being actually worn on a particular part (for example a wrist, a forearm, or the like) of the user's body. In some implementations, the wearing of the mobile terminal may include the terminal body being touched by the user, for example, the driver putting his or her hand on a steering wheel in a state in which the terminal body covers the steering wheel (e.g., the steering wheel cover may include a plurality of sensors).

The wearing of the terminal body may be sensed according to various methods. For example, the watch-type mobile terminal (e.g., smart watch 300 in FIG. 3) may sense whether the terminal body is worn by sensing a tilt and a movement of the terminal body 301. For example, in a case in which a change in a tilt and acceleration according to a movement are identical or similar to patterns when the terminal body 301 is worn on a human body and moved, the watch-type mobile terminal may determine that the terminal body 301 is being worn on a part of the human body. In this example, the terminal body may further include a gyro sensor unit that senses a spatial movement of the terminal based on an x-axis, a y-axis, and a z-axis. As another example, whether the terminal body is worn on a human body may be sensed according to whether one end and the other end of a fastener (e.g., fastener 302a in FIG. 3) included in a band 302 of the terminal body 301 are connected. As another example, after the user wears the terminal body, when the user pushes a particular key or inputs a predetermined voice command, wearing of the terminal body may be sensed.

Although some examples have been described in which a watch-type mobile terminal covers the user's wrist, and it is determined that the user wears the watch-type mobile terminal, implementations are not necessarily limited to a watch-type mobile terminal worn on a user's wrist, as a terminal body may alternatively or additionally be worn on any other part (for example, forearm, head, or the like) of a user in which a bio-signal of the wearer is sensed. In some implementations, the wearing of the terminal body may also include a case in which the mobile terminal is installed in a portion of the vehicle (e.g., a steering wheel of a vehicle) and comes into contact with a user in the vehicle.

When wearing of the terminal body is sensed, the mobile terminal (e.g., a watch-type mobile terminal) may periodically detect a biological signal of the wearer. In some implementations, the biological signal refers to an electrical signal generated by the body of the wearer who wears the watch-type mobile terminal. For example, the biological signal may be any one of an ECG (ElectroCardioGram) signal, a PPG (Photoplethymogram) signal, and a GSR (Galvanic Skin Response) signal, but the present disclosure is not limited thereto and the biological signal may include any type of signal widely used in the art to measure a sleep stage. For example, a body temperature sensor, a pulse sensor, a pressure sensor, or the like, may additionally or alternatively be included.

As a detailed example, major electrical criteria generated by a body of the wearer may include electro-encephalogram (EEG), electrocardiogram (ECG), an electromyogram (EMG), galvanic skin response, or the like, and major physical criteria includes blood pressure, a heart rate, arrhythmia, a stroke quotient, beat defect, a body temperature, a breathing rate, and the like. At least one or more of the major electrical criteria and major physical criteria may be sensed through sensors provided in the watch-type mobile terminal.

In some implementations, an electrocardiogram (ECG) signal is an electrical signal generated from a surface of a skin according to electrical activity of the heart. The ECG signal may be measured by inducing an activity current generated by the heart muscle according to cardiac impulse to two appropriate locations of a body surface.

An electromyogram (EMG) signal is an electrical signal generated from a surface of a skin according to contractile force of muscle, muscle activity, and fatigue of the muscles. EMG may be obtained by sensing a movement of tendons according to a movement of fingers of the wearer sensed when the watch-type mobile terminal (e.g., smart watch 300 in FIG. 3) is worn. In detail, finger flexor tendons of tendons administering movements of fingers exist in a carpal tunnel within a wrist of the terminal wearer. The finger flexor tendons include nine tendons and one nerve, and when a finger is moved, the nine tendons included in the finger flexor tendons are moved in various combinations. A sensing unit (e.g., the sensing unit 140 in FIG. 2) of the mobile terminal may sense a shape of the tendons deformed according to a movement of fingers or the wrist, and a controller (e.g., the controller 180 in FIG. 2) may determine which gesture the fingers make based on the sensed information.

The electroencephalogram (EEG) signal is an electrical signal generated from a surface of the skin according to brain activity with respect to concentration or an external stimulus. The EEG signal may be measured by inducing potential fluctuation that occurs in the cerebrum of a person or a brain current generated according to the potential fluctuation from the scalp.

The GSR signal is an electrical signal generated from a surface of the skin according to a change in skin resistance to activity of the sympathetic nerve. The GSR signal may be obtained by measuring a phenomenon that electrical resistance is temporarily reduced, action potential is generated, and the like, due to an external stimulus or emotional excitement in the skin of a living body.

In some implementations, the body sensor periodically detects a temperature of the wrist of the wearer. In this case, when the terminal body is worn on a body part other than on the wrist, a temperature of the body part on which the terminal body is worn is detected. In a case in which the terminal body is worn on a steering wheel of the vehicle, a temperature of the driver's palm holding the steering wheel is periodically detected.

The GSR sensor detects the amplitude of heart beats transmitted through blood and the muscle distributed in the wrist of the wearer and senses a reaction of the body corresponding to a change in an autonomic nerve. Also, in a case in which the terminal body is worn on the steering wheel, for example, a pressure sensor may obtain state information of the driver through a change in pressure (grasping power or grip) of the driver's hand grasping the wheel.

When an accident is detected, the biological signals collected from the user may be analyzed to determine state information for the user (S330). This analysis may be performed by the mobile terminal that collects the biological signals, or may be performed by another device/system that receives the collected biological signal from the mobile terminal. The analysis of the biological information may be used together with the received vehicle information to determine various types of information about the detected accident, such as, for example, a confirmation of the detected accident, a severity level of the detected accident, etc.

For example, in some implementations, a watch-type mobile terminal may continuously collect a biological signal of a user. When an accident has been detected by the vehicle's e-Call system, the watch-type mobile terminal may receive information about the detected accident from the vehicle's e-Call system. In response to the detected accident event, a controller (e.g., controller 180 in FIG. 2) analyzes the detected biological signal to obtain state information of the wearer. In some implementations, the state information may be discretely categorized, such as by stages, in which different stages represent a different condition of the user.

In some implementations, biological information collected by the mobile terminal and vehicle information collected by the e-Call system may be analyzed in conjunction to detect an accident event, as described next. In some implementations, however, biological information or vehicle information may be analyzed alone to detect an accident event (e.g., if one of the mobile terminal or the e-Call system is inoperable or fails to detect an accident).

In some implementations, a controller (e.g., the controller 180 in FIG. 3) may determine whether a vehicle accident has occurred by combining the received information related to the vehicle and the detected biological signal of the wearer. As a particular example, the controller may first analyze the vehicle information received from the connected e-Call system to determine whether a vehicle accident has occurred and, based on the results of this analysis, use the biological signal to confirm/verify the occurrence of an accident event.

For example, the controller may first determine whether a vehicle accident has occurred according to an operation of the impact sensor of the vehicle, and then confirm that a vehicle accident has occurred based on whether the biological signal of the driver and/or passenger detected before and after the point in time at which the impact sensor detected the accident has suddenly changed. As such, by utilizing both the vehicle information (e.g., from an e-Call system) and biological information of a user, the system may improve accuracy of detecting an accident and reduce occurrences of false alarms in detecting an accident event.

In some implementations, when an accident event of the vehicle is detected based on the received vehicle information (or based on the combination of the received vehicle information and the biological signal of the wearer), the system may output a notification signal. For example, a controller (e.g., the controller 180 in FIG. 2) may output vibrations (or other suitable output) with predetermined patterns through the output unit 150. Accordingly, the wearer of the mobile terminal may immediately recognize occurrence of an accident through the vibrations with the predetermined patterns. In another example, a predetermined announcement voice, instead of vibrations with predetermined patterns, may be output.

In some implementations, the controller may set a plurality of levels corresponding to a change in a detected biological signal to obtain standardized state information of the wearer. For example, the controller may compare a change in value of the biological signal detected before and after a detected accident with one or more threshold values to determine whether the change in biological signal indicates a potential accident event. As a particular example each threshold may correspond to different ranges of change values that indicate different levels of accident severity.

For example, when a change range value of a biological signal detected before and after a detected accident is level 1, the controller may determine that impact is slight, and when the change range value is level 2, the controller may determine that impact is slightly severe, and when the change range value is level 3, the controller may determine that a current state is of emergency. The change range value of a biological signal corresponding to each level may be stored in advance and obtained as necessary. Also, the specific level values and thresholds may be customized for different users. For example, wearer-specific biological signal patterns may be obtained to set personalized baselines values for each user.

In some implementations, the controller may obtain state information of the wearer by stages after detecting an accident by recognizing a change in a level corresponding to a change range value of a biological signal of the wearer. In some implementations, the controller may detect the biological signal of the wearer at predetermined time intervals.

For example, when a change range value of a biological signal detected after detecting an accident is initially level 2 but reduces to level 1 thereafter, the controller may determine that a state of the wearer has been improved. On the other hand, after detecting an accident, if a change range value of a biological signal is initially level 1 and increases to level 2 thereafter, the controller may determine that a state of the wearer has been aggravated.

In this manner, when state information of the wearer is obtained and a predetermined condition is met (e.g., a worsening condition of a person in the vehicle), the controller interworks with the e-Call system and transmits the obtained state information of the wearer and the information related to a state of the vehicle to the predetermined call center (step S340).

Here, the predetermined condition refers to a case in which a degree of impact corresponding to the state information of the wearer obtained at the timing of detecting the accident exceeds a predetermined reference range or a case in which a degree of impact corresponding to the information related to the state of the vehicle received at the timing of the occurrence of the accident exceeds a predetermined reference range.

For example, in case of a minor collision, the system may determine that there is no need to connect a call to the call center. Thus, such a case may be excluded to reduce the number of unnecessary emergency calls, thus increasing user convenience. However, even in such a case, information regarding the user and/or the vehicle may still be transmitted to the call center by performing inputting on the e-Call system or the watch-type mobile terminal 100 or the call center may be connected.

In some implementations, other devices/systems may be contacted in addition, or as an alternative, to an e-Call center. For example, in a case in which an emergency signal included in the obtained state information of the wearer is sensed, a controller (e.g., controller 180 in FIG. 2) may provide control such that a terminal at a location nearest to a current location of the wearer may be contacted (or connected) using, for example, a GPS or a base station. As a specific example, in a case in which the wearer is in an emergency situation, a terminal of a different user nearest to the location of the current vehicle may be contacted through a GPS or a base station, whereby the wearer may receive help from someone else or quickly cope with the situation at an early stage until a rescue vehicle arrives.

The controller may output various types of information upon detecting an accident, such as a time at which the accident has occurred, the information related to a state of the vehicle received at the timing of the accident, and the obtained state information of the wearer of the wearable device. For example, such information may be displayed to a display unit (e.g., the display unit 351 in FIG. 3). Accordingly, the wearer of the wearable device (or any other user) may directly view information related to an accident situation.

As described above, in some implementations, a mobile terminal (e.g., mobile terminal 100 in FIG. 2), which can be a wearable device such as a watch-type terminal (e.g., smart watch 300 in FIG. 3) interworks with the e-Call system of the vehicle, so that when a vehicle accident occurs, the mobile terminal 100 interworking with the e-Call system of the vehicle may transmit information regarding a state of the vehicle or state information obtained through a biological signal of a driver or a passenger in the vehicle to a call center, so that the driver or the passenger may be provided with an emergency treatment appropriate for the situation.

The flow chart in FIG. 5 illustrated an example of establishing a connection between a user's mobile terminal and a vehicle's e-Call system and analyzing information regarding the user and the vehicle. In the example of FIG. 5, the mobile terminal analyzes the user's information and/or the vehicle's information, and contacts a call center when a predetermined condition is satisfied. Other variations are possible. For example, in some implementations, the analysis of the user's information and/or the vehicle's information may be performed by devices/systems other than the mobile terminal, such as the vehicle's e-Call system or an external call center, as described next.

Figure 6:
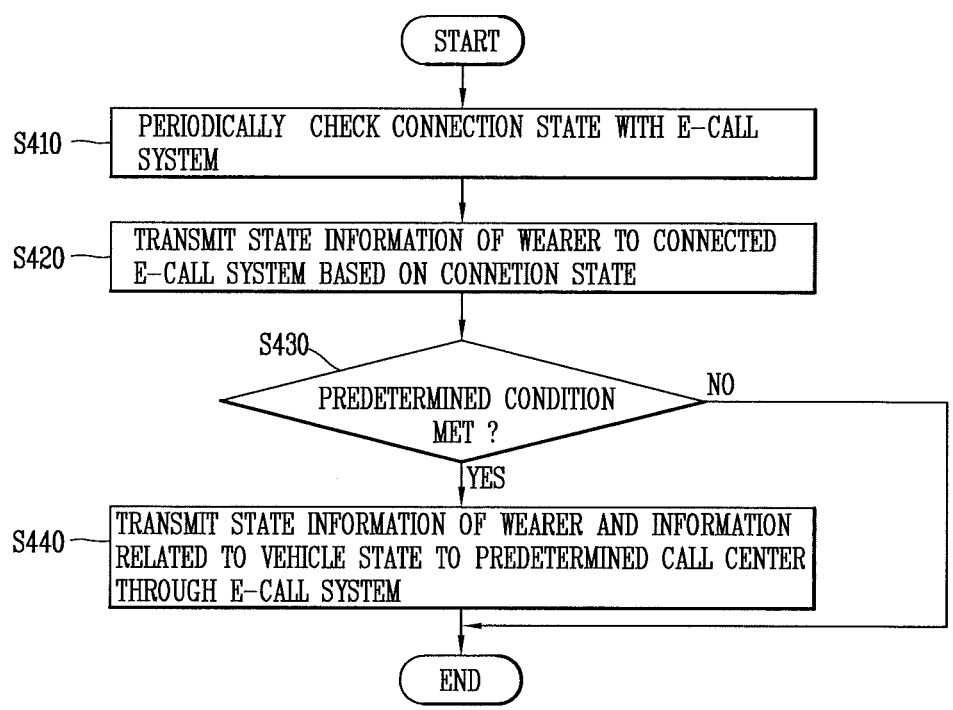
Figure 7:
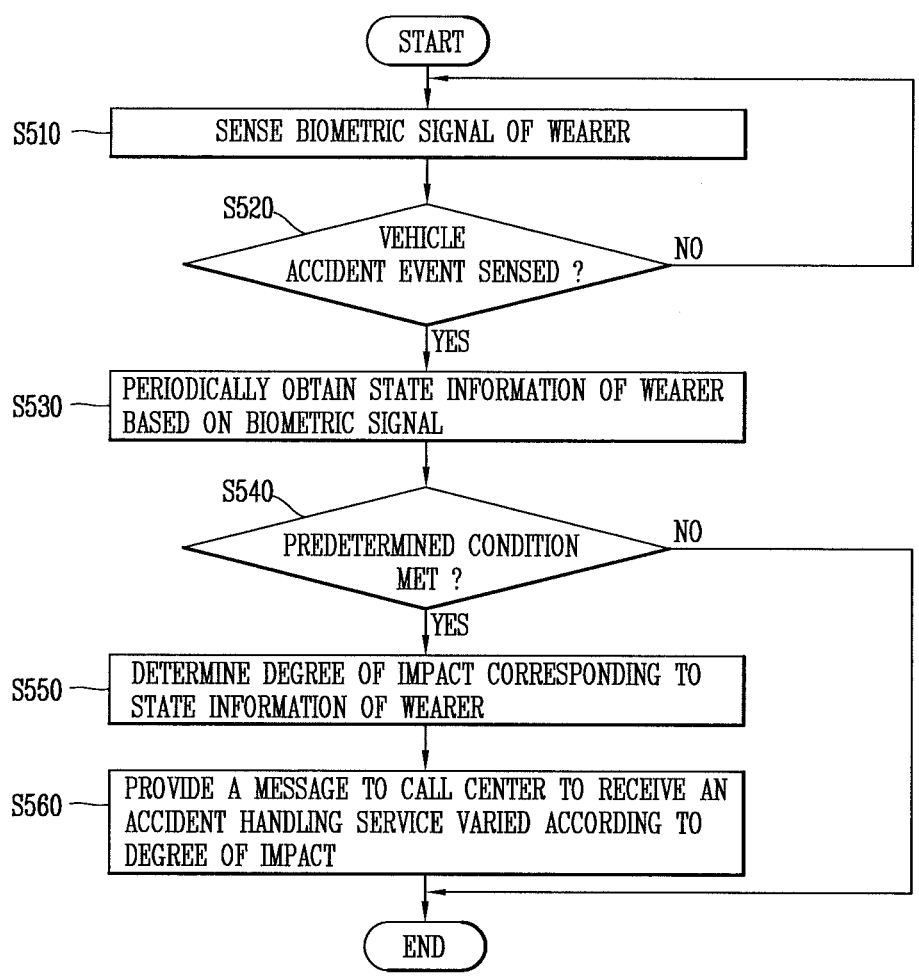
Figure 8:
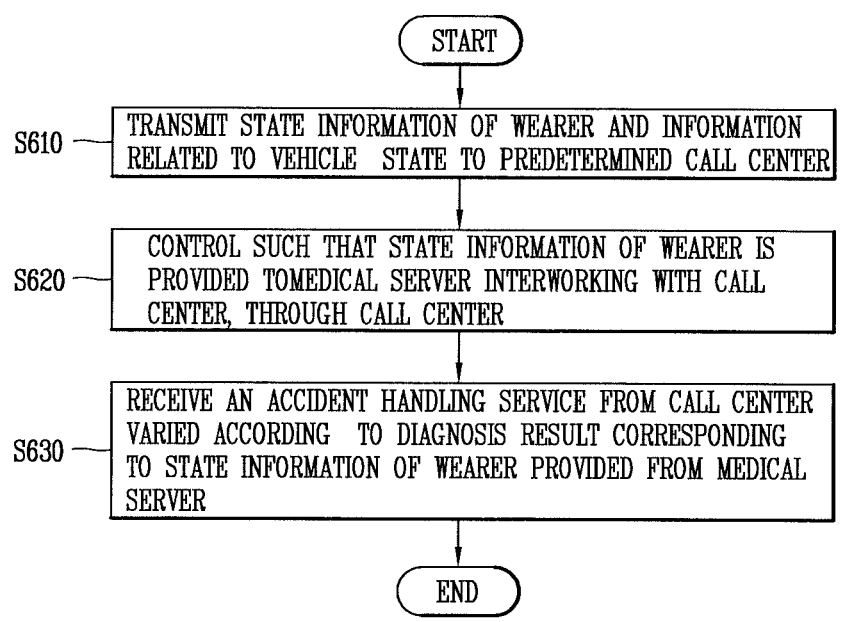

FIGS. 6 through 8 are flow charts illustrating other examples of handling a vehicle accident using a mobile terminal and an e-Call system.

FIG. 6 is a flow chart illustrating an example of performing various operations according to a connection state between a mobile terminal (e.g., the mobile terminal 100 in FIG. 1 or FIG. 2) and the e-Call system (e.g., e-Call system 20 in FIG. 1). In this example, the mobile terminal (e.g., the smart watch 300 in FIG. 3) continuously collects a user's biological information and transmits a state of the user to the vehicle's e-Call system, which analyzes the information along with the vehicle's information, and contacts a call center when a predetermined condition is satisfied.

The watch-type mobile terminal may initially be connected to the e-Call system of the vehicle either automatically or through a predetermined input. For example, when a predetermined input applied to a display unit (e.g., the display unit 351 in FIG. 3) of the watch-type mobile terminal is sensed, or when the driver who wears the watch-type mobile terminal enters a vehicle, the watch-type mobile terminal and the vehicle's e-Call system may be connected. The connection between the watch-type mobile terminal and the vehicle's e-Call system may be performed using, for example, a near-field communication standard such as Bluetooth, or the like, a wireless Internet standard such as Wi-Fi, or the like, an external device interface standard such as a universal serial bus (USB), or the like.

In the example of FIG. 6, after the watch-type mobile terminal and the vehicle's e-Call system are connected, a controller (e.g., controller 180 in FIG. 2) periodically checks the connection state (step S410).

The connection state may be recognized, for example, through signal strength, a change in a communication speed, and the like, exchanged between the watch-type mobile terminal and the vehicle's e-Call system. Also, the connection state may be output through an image, an icon, or the like, corresponding to a display unit (e.g., the display unit 351 in FIG. 3) of the watch-type mobile terminal.

In some implementations, when the connection state is weak, the controller may change the connection state so that the watch-type mobile terminal and the vehicle's e-Call system are connected through a different communication path. For example, the controller may change the connection state by alternating Bluetooth low energy (BLE), Bluetooth telecommunication (BT), Wi-Fi communication, and the like, according to a current connection state.

In the example process of FIG. 6, the controller transmits state information of the terminal wearer to the vehicle's e-Call system, based on the connection state (step S420). In some implementations, the controller performs synchronization between the mobile terminal and the e-Call system. The synchronization may, for example, facilitate the establishment of the connection and help reduce occurrences of dropped connections that may result in the state information of the vehicle driver or the passenger not being transferred to the call center through the terminal.

Thereafter, the system may detect that a predetermined condition has occurred (step S430). As described with reference to FIG. 5, above, the predetermined condition may be, for example, a worsening condition of a user or the vehicle. As a specific example, the predetermined condition may correspond to a degree of impact corresponding to the state information of the wearer exceeding a predetermined reference range or a degree of impact corresponding to the information related to the state of the vehicle exceeding a predetermined reference range.

After the predetermined condition is detected, the controller transmits the state information of the wearer and the information related to a state of the vehicle to the predetermined call center through the e-Call system (step S440).

As described above, even when the connection state between the mobile terminal and the vehicle's e-Call system is released (e.g., due to operation incapability of the e-Call system), the mobile terminal may adapt the communication state so that an external call center may still be contacted and an accident handling service may be received. As a particular example, through periodic synchronization between the watch-type mobile terminal and the vehicle's e-Call system, information related to a state of the vehicle and the state information of the driver or the passenger may be transmitted to the call center through the mobile terminal.

In some implementations, the mobile terminal may change the connection state to the vehicle's e-Call system for other reasons, such as based on the type of data to be transmitted or communication requirements to the e-Call system.

As a specific example, the watch-type mobile terminal may receive image data captured before or after the accident event from the connected vehicle's e-Call system. In this example, the watch-type mobile terminal may change a communication path corresponding to the connection state to transmit the image. For example, in a case in which the watch-type mobile terminal and the e-Call system are connected through Bluetooth low energy (BLE), the available communication resources may not be sufficient to transmit image data having large capacity. In such cases, the mobile terminal may change the communication path (e.g., to Bluetooth telecommunication (BT) or Wi-Fi communication, etc.) and image data captured before or after the accident event may be subsequently received.

In the example of FIG. 6, when the predetermined condition is detected (e.g., a worsening condition of the user and/or the vehicle), the received image data is transmitted together with the state information of the wearer and the information related to a state of the vehicle to a predetermined call center.

FIG. 7 is a flow chart illustrating another example of receiving a service varied according to a degree of impact included in the state information of the wearer obtained through the watch-type mobile terminal.

When the watch-type mobile terminal and the e-Call system of the vehicle are connected, the terminal may receive information related to the state of the vehicle from the connected e-Call system. The information related to the state of the vehicle may include, for example, inflation of an airbag device, a sensor value sensed by an impact sensor, as well as location information of the vehicle using a GPS, a predetermined destination, running route information, etc.

When the terminal body is worn, a biological signal of the wearer or a change in a biological signal is sensed by one or more of various sensors, for example, a GSR sensor, a body temperature sensor, a pulse sensor, and/or a pressure sensor (step S510). The sensing may be performed continuously, periodically, or with any suitable frequency.

Thereafter, a controller (e.g., the controller 180 in FIG. 2) senses an accident event of the vehicle (step S520). The accident may be detected, for example, based on the information related to the state of the vehicle received from the e-Call system and/or based on the biological signal of the wearer.

When an accident event of the vehicle is sensed, state information of the wearer is periodically obtained based on the biological signal of the wearer (step S530). As a specific example, after the accident event is sensed, a degree of change in a biological signal of the wearer is continuously monitored at predetermined time intervals.

Thereafter, the controller determines whether the obtained state information of the wearer and/or the received information related to a state of the vehicle meet a predetermined condition (step S540). In some implementations, the state information of the wearer corresponding to the predetermined condition is a condition for requesting an emergency rescue from the call center, which may be a one-time impact value. As a specific example, when the obtained state information of the wearer satisfies a predetermined threshold value, the system may determine that the predetermined condition is satisfied.

After the system determines that the predetermined condition is satisfied, the system may determine a degree of impact corresponding to the state information of the wearer (step S550). In some implementations, a degree of impact corresponding to the state information of the wearer in step S550 refers to an impact change value continuously measured even when the predetermined threshold value in step S540 is satisfied. Thus, through the step S550, even a call center (or any other emergency rescue agency, or the like) that is distant from an accident scene may accurately recognize a change in a state of the driver or the passenger, and provide a customized emergency rescue.

Thereafter, the controller provides a message to a call center so as to receive an accident handling service varied according to a degree of impact corresponding to step S550 (S560).

As a detailed example, after an accident event of the vehicle is sensed, the system may detect that an abnormal signal of the state information of the wearer obtained at a second point in time has increased to be greater than the state information of the wearer obtained at a first point in time. Based on this increase of the abnormal signal, the controller may transmit a message to stop operation of the vehicle to the predetermined call center. To this end, the controller may sense whether the vehicle has continued to operate after the accident based on the information related to a state of the vehicle received from the e-Call system after the accident occurs.

In this example, the first point in time refers to a point in time close to a point in time at which the accident occurred, compared to the second point in time, and the second point in time refers to a point which has lapsed from the first point in time. Also, the abnormal signal may indicate that the state of the driver or the passenger in the vehicle becomes aggravated after the accident occurs, and may include, for example, an increase in the number of cardiac impulse, an increase in a change in a body temperature, an increase in a change in pulsation, and the like.

Meanwhile, even after the message inducting stopping running of the vehicle is transmitted, when the running of the vehicle is not stopped, the watch-type mobile terminal may operate such that the vehicle is controlled through the interworking e-Call system.

In some implementations, after the accident event of the vehicle is sensed, if the controller detects that a user's condition is stabilized or improving, then the controller may take less severe actions in response. For example, if the abnormal signal of the state information of the wearer obtained at the second point in time has been maintained or is reduced, compared to the state information of the wearer obtained at the first point in time, the controller may transmit a message to provide information regarding a medical institution located near the current location of the vehicle to the predetermined call center.

In this manner, after an accident has been detected, the state information of the driver or the passenger of the vehicle is provided (e.g., classified in discrete stages indicating different levels of severity of the user's condition) to the call center, and thus, an emergency rescue service may be appropriately varied according to a change in the state of the driver or the passenger. Accordingly, a useful, reliable customized emergency rescue appropriate for a situation may be made.

Turning now to FIG. 8, an example of receiving a reliable accident handling service by providing state information of a vehicle driver or a passenger to the outside before an emergency rescue is made is described. The steps in FIG. 8 may be performed, for example, after the predetermined condition in step S340 illustrated in FIG. 5 is met.

In some implementations, a watch-type mobile terminal (e.g., smart watch 300 in FIG. 3) transmits state information of the wearer and information related to a state of the vehicle to the predetermined call center (step S610).

Next, the controller provides control such that the state information of the wearer is provided to a medical server (e.g., medical server 70 in FIG. 1) interworking with the call center through the call center (step S620). To this end, when information is transmitted to the call center in step S610, a control signal may be included that requests providing the state information of the wearer to the medical server that interworks with the call center. When such a request signal is included, the call center may provide the state information (or the biological signal) of the wearer to the medical server (e.g., medical server 70 as illustrated in FIG. 1).

The state information of the wearer may be analyzed at the medical server, and diagnosis results corresponding to the state information of the wearer are provided from the medical server to the call center. The watch-type mobile terminal may then receive an accident handling service that is varied according to the diagnosis results (step S630).

In this manner, through the medical server that interworks with the call center, initial diagnosis may be promptly performed on the person in the accident, thus receiving reliable customized emergency rescue service.

As described above, in the mobile terminal and the method for handling an accident of a vehicle, when an accident of a vehicle is sensed, information regarding a state of the vehicle and a biological signal of a driver or a passenger within the vehicle are transmitted to a call center, by interworking with the e-Call system of the vehicle, and thus, an emergency treatment according to a situation may be received. Also, after the accident, state information of the driver or the passenger within the vehicle is continuously provided to the call center (e.g., classified according to discrete stages indicating different levels of severity), and thus, an emergency rescue service varied according to a change in a state of the driver or the passenger may be received. Thus, useful, reliable customized emergency rescue that fits a situation may be provided.

In some implementations, the foregoing method may be implemented as codes that can be read by a computer in a program-recorded medium. The computer-readable medium may include any types of recording devices in which data that can be read by a computer system is stored. The computer-readable medium may include a ROM, a RAM, a CD-ROM, a magnetic tape, a floppy disk, an optical data storage device, and the like. The processor-readable medium also includes implementations in the form of carrier waves or signals (e.g., transmission via the Internet). Also, the computer may include a controller (e.g., the controller 180 in FIG. 2) of the mobile terminal.

Implementations can be readily applied to other types of methods and apparatuses. This description is intended to be illustrative, and not to limit the scope of the claims. Many alternatives, modifications, and variations will be apparent to those skilled in the art. The features, structures, methods, and other characteristics of the implementations described herein may be combined in various ways to obtain additional and/or alternative implementations.

Mobile terminals presented herein may be implemented using a variety of different types of terminals. Examples of such terminals include cellular phones, smart phones, user equipment, laptop computers, digital broadcast terminals, personal digital assistants (PDAs), portable multimedia players (PMPs), navigators, portable computers (PCs), slate PCs, tablet PCs, ultra books, wearable devices (for example, smart watches, smart glasses, head mounted displays (HMDs)), and the like.

The methods, techniques, systems, and apparatuses described herein may be implemented in digital electronic circuitry or computer hardware, for example, by executing instructions stored in tangible computer-readable storage media.

Apparatuses implementing these techniques may include appropriate input and output devices, a computer processor, and/or tangible computer-readable storage media storing instructions for execution by a processor.

A process implementing techniques disclosed herein may be performed by a processor executing instructions stored on a tangible computer-readable storage medium for performing desired functions by operating on input data and generating appropriate output. Suitable processors include, by way of example, both general and special purpose microprocessors. Suitable computer-readable storage devices for storing executable instructions include all forms of non-volatile memory, including, by way of example, semiconductor memory devices, such as Erasable Programmable Read-Only Memory (EPROM), Electrically Erasable Programmable Read-Only Memory (EEPROM), and flash memory devices; magnetic disks such as fixed, floppy, and removable disks; other magnetic media including tape; and optical media such as Compact Discs (CDs) or Digital Video Disks (DVDs). Any of the foregoing may be supplemented by, or incorporated in, specially designed application-specific integrated circuits (ASICs).

Although the operations of the disclosed techniques may be described herein as being performed in a certain order and/or in certain combinations, in some implementations, individual operations may be rearranged in a different order, combined with other operations described herein, and/or eliminated, and desired results still may be achieved. Similarly, components in the disclosed systems may be combined in a different manner and/or replaced or supplemented by other components and desired results still may be achieved.

What is claimed is:

1. A mobile terminal comprising:
  a terminal body configured to be wearable on a part of a user's body;
  a wireless communication unit configured to connect to an e-Call system of a vehicle when the user wearing the terminal body enters the vehicle and to receive information related to a state of the vehicle;
  a detecting unit configured to detect a biometric signal of the user that is sensed by at least one sensor provided in the terminal body; and
  a controller configured to:

based on an accident event of the vehicle being detected from the received information related to the state of the vehicle, analyze the detected biometric signal to obtain state information of the user, based on a predetermined condition being satisfied, cooperate with the e-Call system of the vehicle and transmit the obtained state information of the user and the information related to a state of the vehicle to a call center, periodically obtain, based on the detected biometric signal, state information of the user after transmitting, to the call center, first state information of the user obtained at a first point in time after the accident event of the vehicle was detected, compare the first state information of the user obtained at the first point in time with second state information of the user obtained at a second point in time, the second point in time occurring after the first point in time, and based on results of comparing the first state information with the second state information, request a varied accident handling service to the call center, wherein based on detecting that an abnormal signal of state information of the user obtained at the second point in time is smaller than an abnormal signal of state information of the user obtained at the first point in time, information regarding a medical institution nearest to a current location of the vehicle is provided.

2. The mobile terminal of claim 1, wherein the predetermined condition comprises a condition in which a degree of impact corresponding to the obtained state information of the user exceeds a predetermined reference range or a condition in which a degree of impact corresponding to the received information related to a state of the vehicle exceeds a predetermined reference range.

3. The mobile terminal of claim 1, wherein the controller is further configured to:
periodically check a state of connection with the e-Call system;
perform synchronization with the e-Call system; and
based on a state of the connection, provide the obtained state information of the user to the connected e-Call system.

4. The mobile terminal of claim 1, wherein the controller is configured to, based on an emergency signal included in the obtained state information of the user being detected, control the wireless communication unit to contact an external terminal nearest to a current location of the user by using a global positioning system (GPS) or a base station (BS).

5. The mobile terminal of claim 1, wherein the controller is configured to, according to the results of comparing the first state information with the second state information, based on an abnormal signal of state information of the user obtained at the second point in time being greater than an abnormal signal of state information of the user obtained at the first point in time, transmit a message to the call center to induce the vehicle to stop running.

6. The mobile terminal of claim 1, wherein the wireless communication unit is further configured to receive, from the connected e-Call system, image data that was imaged before and after the detected accident event, and
the controller is further configured to, based on the predetermined condition being satisfied, transmit the state information of the user, the information related to a state of the vehicle, and the received image data to the call center.

7. The mobile terminal of claim 1, wherein the at least one sensor provided in the terminal body includes at least one or more of a galvanic skin response (GSR) sensor, a body temperature sensor, a pulse sensor, or a pressure sensor.

8. The mobile terminal of claim 1, wherein the controller is configured to detect an accident event by performing operations comprising:
determining whether the vehicle has been in an accident based on the received information related to a state of the vehicle, and
in response to determining that the vehicle has been in an accident based on the received information related to a state of the vehicle, confirming that the vehicle has been in an accident using the biometric signal.

9. The mobile terminal of claim 1, further comprising:
an output unit provided in the terminal body and configured to output vibrations,
wherein the controller is configured to, in response to the accident event of the vehicle being detected based on the received information, control the output unit to output a vibration with a predetermined pattern.

10. The mobile terminal of claim 1, wherein the controller is further configured to:
provide a control signal such that the state information of the user is provided, through the call center, to a medical server that interworks with the call center, and
receive an accident handling service that is varied according to diagnosis results provided by the medical server based on the state information of the user.

11. The mobile terminal of claim 1, wherein the state information of the user is represented by a plurality of stages indicating different levels of severity.

12. The mobile terminal of claim 1, wherein the predetermined condition comprises a condition in which the state information of the user indicates an emergency situation and the received information related to a state of the vehicle does not indicate an accident of the vehicle, and the mobile terminal is configured to transmit a message to an external device to the vehicle based on the state information of the user indicating an emergency situation.

13. The mobile terminal of claim 12, wherein the external device to the vehicle is a mobile device of another user.

14. A method for handling an accident of a vehicle, the method comprising:
connecting a mobile terminal to an e-Call system of a vehicle when a user wearing the mobile terminal enters the vehicle, and receiving, at the mobile terminal, information related to a state of the vehicle from the e-Call system;
detecting a biometric signal of the user who is wearing the mobile terminal;
based on an accident event of the vehicle being detected from the received information related to a state of the vehicle, analyzing the detected biometric signal of the user to obtain state information of the user;
based on a predetermined condition being satisfied by the obtained state information of the user and the information related to a state of the vehicle, transmitting to a call center, by the mobile terminal in cooperation with the e-Call system, the obtained state information of the user and the information related to a state of the vehicle;
periodically obtaining, based on the detected biometric signal, state information of the user after transmitting, to the call center, first state information of the user obtained at a first point in time after the accident event of the vehicle was detected;

comparing the first state information of the user obtained at the first point in time with second state information of the user obtained at a second point in time, the second point in time occurring after the first point in time; and based on results of comparing the first state information with the second state information, requesting a varied accident handling service to the call center, wherein based on detecting that an abnormal signal of state information of the user obtained at the second point in time is smaller than an abnormal signal of state information of the user obtained at the first point in time, information regarding a medical institution nearest to a current location of the vehicle is provided.

15. The method of claim 14, wherein the predetermined condition comprises a condition in which a degree of impact corresponding to the obtained state information of the user exceeds a predetermined reference range or a condition in which a degree of impact corresponding to the received information related to a state of the vehicle exceeds a predetermined reference range.

16. The method of claim 14, further comprising:
periodically checking a state of connection with the e-Call system;
performing synchronization with the e-Call system; and
based on a state of the connection, providing the obtained state information of the user to the connected e-Call system.

17. A system comprising:
an e-Call system installed in a vehicle;
a mobile terminal configured to be wearable on a part of a user's body, wherein the mobile terminal comprises a wireless communication unit configured to connect to the e-Call system of the vehicle when the user wearing the mobile terminal enters the vehicle and to receive information related to a state of the vehicle, and a detecting unit configured to detect a biometric signal of the user; and
a controller configured to:
responsive to an accident event of the vehicle being detected from the received information related to a state of the vehicle, obtain state information of the user based on analyzing the biometric signal detected by the detecting unit of the mobile terminal,
determine that a predetermined condition is satisfied by at least one of the state information of the user or the received information related to the state of the vehicle,
based on determining that the predetermined condition is satisfied, cooperate with the e-Call system of the vehicle and transmit, to a call center, at least one of the state information of the user or the information related to a state of the vehicle,
periodically obtain, based on the detected biometric signal, state information of the user after transmitting, to the call center, first state information of the user obtained at a first point in time after the accident event of the vehicle was detected,
compare the first state information of the user obtained at the first point in time with second state information of the user obtained at a second point in time, the second point in time occurring after the first point in time, and
based on results of comparing the first state information with the second state information, request a varied accident handling service to the call center,
wherein based on detecting that an abnormal signal of state information of the user obtained at the second point in time is smaller than an abnormal signal of state information of the user obtained at the first point in time, information regarding a medical institution nearest to a current location of the vehicle is provided.

18. The system of claim 17, further comprising a second mobile terminal configured to be wearable on a part of a second user's body, wherein the second mobile terminal comprises:
a second wireless communication unit configured to connect to the e-Call system of the vehicle and receive information related to a state of the vehicle; and
a second detecting unit configured to detect a biometric signal of the second user,
wherein the controller is further configured to analyze the biometric signal of the second user to determine state information of the second user, and wherein the predetermined condition further depends on the state information of the second user.

* * * * *